United States Patent
Wu et al.

(10) Patent No.: US 11,534,068 B2
(45) Date of Patent: Dec. 27, 2022

(54) SYSTEMS AND METHODS FOR DETERMINING A TARGET POSITION OF A SCANNING TABLE

(71) Applicant: SHANGHAI UNITED IMAGING HEALTHCARE CO., LTD., Shanghai (CN)

(72) Inventors: Dong Wu, Shanghai (CN); Zhiguo Zhang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 1045 days.

(21) Appl. No.: 16/101,406

(22) Filed: Aug. 11, 2018

(65) Prior Publication Data

US 2019/0046131 A1 Feb. 14, 2019

(30) Foreign Application Priority Data

Aug. 11, 2017 (CN) .......................... 201710686196.8
Feb. 8, 2018 (CN) .......................... 201810129846.3

(51) Int. Cl.
| | |
|---|---|
| *A61B 5/00* | (2006.01) |
| *A61B 6/04* | (2006.01) |
| *G01R 33/54* | (2006.01) |
| *A61B 6/03* | (2006.01) |
| *A61B 5/055* | (2006.01) |

(Continued)

(52) U.S. Cl.
CPC ............ *A61B 5/0037* (2013.01); *A61B 5/055* (2013.01); *A61B 5/704* (2013.01); *A61B 6/037* (2013.01); *A61B 6/04* (2013.01); *A61B 6/0407* (2013.01); *A61B 6/0492* (2013.01);

(Continued)

(58) Field of Classification Search
CPC ......... A61B 5/00; A61B 5/0037; A61B 5/055; A61B 5/704; A61B 6/037; A61B 6/04; A61B 6/0407; A61B 6/0492; A61B 6/54; G16H 40/60; G01R 33/543; G01R 33/58
See application file for complete search history.

(56) References Cited

U.S. PATENT DOCUMENTS

2007/0225588 A1 9/2007 Steckner
2010/0194390 A1* 8/2010 Kannengiesser ........................... G01R 33/56375
324/309

(Continued)

FOREIGN PATENT DOCUMENTS

| CN | 103054579 A | 4/2013 |
|---|---|---|
| CN | 103385728 A | 11/2013 |

(Continued)

OTHER PUBLICATIONS

First Office Action in Chinese Application No. 201710686196.8 dated Nov. 14, 2019, 30 pages.

(Continued)

*Primary Examiner* — Fredrick C Conley
(74) *Attorney, Agent, or Firm* — Metis IP LLC

(57) ABSTRACT

A system and method for positioning a scanning table are provided. The method may include obtaining a body length of an object; and determining the number of table positions for scanning the object based on a length of each scanning region of the scanning table, an initial length of an overlapping region of the scanning table at two adjacent table positions, and the body length of the object.

20 Claims, 13 Drawing Sheets

(51) Int. Cl.
*G16H 40/60* (2018.01)
*A61B 6/00* (2006.01)
*G01R 33/58* (2006.01)

(52) U.S. Cl.
CPC ........... *G01R 33/543* (2013.01); *G16H 40/60* (2018.01); *A61B 6/54* (2013.01); *G01R 33/58* (2013.01)

(56) References Cited

U.S. PATENT DOCUMENTS

| | | | |
|---|---|---|---|
| 2011/0190620 A1* | 8/2011 | Oda | A61B 5/055 600/410 |
| 2015/0073255 A1 | 3/2015 | Liu et al. | |
| 2015/0265226 A1* | 9/2015 | Jackson | A61B 6/032 378/16 |
| 2016/0223633 A1 | 8/2016 | Xiong et al. | |
| 2017/0084057 A1 | 3/2017 | Li et al. | |
| 2017/0103551 A1 | 4/2017 | Sun et al. | |
| 2017/0160353 A1 | 6/2017 | Gu et al. | |
| 2020/0245894 A1* | 8/2020 | Shi | A61B 5/055 |

FOREIGN PATENT DOCUMENTS

| | | |
|---|---|---|
| CN | 103908251 A | 7/2014 |
| CN | 104644171 A | 5/2015 |
| CN | 104679744 A | 6/2015 |
| CN | 105078495 A | 11/2015 |
| CN | 106368851 A | 2/2017 |
| CN | 106772157 A | 5/2017 |
| CN | 107065860 A | 6/2017 |
| CN | 106932742 A | 7/2017 |
| CN | 103908251 B | 11/2017 |
| CN | 105893772 B | 9/2018 |
| JP | 2007159719 A | 6/2007 |
| JP | 2011000134 A | 1/2011 |

OTHER PUBLICATIONS

First Office Action in Chinese Application No. 201810129846.3 dated Dec. 22, 2020, 22 pages.
Dong, Ye, Utility of 18F-FDG PET/CT in the Diagnosis of Non-Small Cell Lung Cancer, China Master's Theses Full-text Database, Medical and Health Technology Series, vol. 1, 2015, 17 pages.

* cited by examiner

SYSTEMS AND METHODS FOR DETERMINING A TARGET POSITION OF A SCANNING TABLE

CROSS-REFERENCE TO RELATED APPLICATIONS

This application claims priority to Chinese Patent Application No. 201710686196.8, filed on Aug. 11, 2017, and Chinese Patent Application No. 201810129846.3, filed on Feb. 8, 2018, the contents of which are incorporated herein by reference.

TECHNICAL FIELD

The present disclosure generally relates to systems and methods for imaging, and in particular, to systems and methods for determining a target position of a scanning table of an imaging device.

BACKGROUND

In an imaging system, in order to obtain a clear and accurate image, the scanning center of an imaging device and the center of a scanning region of an object (e.g., a patient) need to be aligned (i.e., the scanning table of the imaging device needs to be positioned, or one or more target positions of the scanning table need to be determined) before scanning. The scanning table can be positioned based on a coil located in a fixed position of the imaging device. However, the position of the coil may vary in the operation. Therefore, it is difficult to automatically positioning the scanning table based on a coil having a variable position. The scanning table can also be positioned using a laser lamp mounted on the imaging device. For example, the positioning of the scanning table can be adjusted to make a laser beam emitted from the laser lamp irradiate a target position (e.g., a position to be scanned by the imaging device) of the object. Generally, the operation needs to be repeated for two or more times to position the scanning table using the laser lamp, increasing the complexity of the operation and influencing the efficiency of the positioning of the scanning table. Thus, it is desirable to develop systems and methods for positioning the scanning table automatically.

SUMMARY

In one aspect of the present disclosure, a method for positioning a scanning table is provided. The method may be implemented on at least one computing device, each of which has at least one processor and a storage. The method may include one or more of the following operations: obtaining a body length of an object; and/or determining the number of table positions for scanning the object based on a length of each scanning region of the scanning table, an initial length of an overlapping region of the scanning table at two adjacent table positions, and/or the body length of the object.

In some embodiments, the method may further include one or more of the following operations: determining an effective length of the overlapping region of the scanning table at two adjacent table positions based on the number of the table positions and the body length of the object; and/or adjusting the overlapping region of the scanning table at two adjacent table positions based on the effective length of the overlapping region.

In some embodiments, the method may further include one or more of the following operations: obtaining positioning information of the object on the scanning table; determining a scanning direction for scanning the object based on the positioning information; determining a scanning region of the object corresponding to each table position based on the scanning direction, the number of the table positions, and/or a first predetermined relationship between a plurality of scanning regions of one or more objects and a plurality of corresponding table positions; and/or setting a scanning protocol at each table position based on the scanning region of the object corresponding to the each table position.

In some embodiments, the predetermined relationship between a plurality of scanning region of one or more objects and a plurality of corresponding table positions may be denoted by a first lookup chart.

In some embodiments, the first lookup chart may include a correspondence between the body length of the object, the number of the table positions, and/or a length of each scanning region of the object.

In some embodiments, the setting of a scanning protocol at each table position based on the scanning region of the object corresponding to the each table position may include one or more of the following operations: determining a scanning protocol for the scanning region of the object corresponding to the each table position based on the scanning region of the object corresponding to the each table position, and/or a second predetermined relationship between a plurality of scanning regions of one or more objects and a plurality of corresponding scanning protocols; and/or setting the scanning protocol at the each table position based on the each determined scanning protocol for the scanning region of the object corresponding to the each table position.

In some embodiments, the second predetermined relationship between a plurality of scanning regions of one or more objects and a plurality of corresponding scanning protocols may be denoted by a second lookup chart.

In some embodiments, the determination of the number of table positions for scanning the object based on a length of a scanning region of the scanning table, an initial length of an overlapping region of the scanning table at two adjacent table positions, and/or the body length of the object may include one or more of the following operations: determining the number of the table positions for scanning the object based on the following equation:

$$couchsize = \text{ceil}\left(\frac{\text{height} + \text{length} * overlap_{min}}{\text{length} * (1 - overlap_{min})}\right),$$

wherein couchsize may refer to the number of the table positions for scanning the object, the cell function may refer to a determination of a minimum integer that is greater than or equal to $$\frac{\text{height} + \text{length} * overlap_{min}}{\text{length} * (1 - overlap_{min})},$$

height may refer to the body length of the object, length may refer to the length of each scanning region of the scanning table, and $overlap_{min}$ may refer to the initial length of an overlapping region of the scanning table at two adjacent table positions.

In some embodiments, the determination of an effective length of the overlapping region of the scanning table at two adjacent table positions based on the number of the table positions and the body length of the object may include one or more of the following operations: determining an estimated length of the overlapping region based on the number of the table positions, the body length of the object, the length of each scanning region of the scanning table, a first distance between a head of the object and an end of a corresponding table position, and/or a second distance between a foot of the object and an end of a corresponding table position; and/or determining the effective length of the overlapping region based on the estimated length of the overlapping region or the initial length of the overlapping region.

In some embodiments, the determination of the effective length of the overlapping region based on the estimated length of the overlapping region or the initial length of the overlapping region may include one or more of the following operations: determining whether the estimated length of the overlapping region is greater than or equal to the initial length of the overlapping region; and/or in response to a determination that the estimated length of the overlapping region is greater than or equal to the initial length of the overlapping region, designating the estimated length of the overlapping region as the effective length of the overlapping region.

In some embodiments, the determination of the effective length of the overlapping region based on the estimated length of the overlapping region or the initial length of the overlapping region may include one or more of the following operations: determining whether the estimated length of the overlapping region is greater than or equal to the initial length of the overlapping region; and/or in response to the determination that the estimated length of the overlapping region is smaller than the initial length of the overlapping region, designating the initial length of the overlapping region as the effective length of the overlapping region.

In another aspect of the present disclosure, a method for determining a target position of a scanning table of an imaging device is provided. The method may be implemented on at least one computing device, each of which has at least one processor and a storage. The method may include one or more of the following operations: obtaining a scanning calibration sequence; determining a sensitivity distribution of a surface coil of the imaging device based on the scanning calibration sequence; determining a center position of the surface coil based on the sensitivity distribution; and/or determining the target position of the scanning table based on the center position of the surface coil. In some embodiments, the target position of the scanning table may correspond to the center position of the surface coil when the center position of the surface coil is located coincident with a scanning center of the imaging device.

In some embodiments, the surface coil may include at least one coil unit, and the determination of a sensitivity distribution of a surface coil based on the scanning calibration sequence may include one or more of the following operations: obtaining a first signal of each coil unit of the at least one coil unit generated based on the scanning calibration sequence; obtaining a second signal of a volume coil of the imaging device generated based on the scanning calibration sequence; determining a first signal intensity distribution of the each coil unit of the at least one coil unit based on the first signal; determining a second signal intensity distribution of the volume coil of the imaging device based on the second signal; and/or obtaining the sensitivity distribution of the each coil unit by fusing the first signal intensity distribution of the each coil unit and the second signal intensity distribution.

In some embodiments, the surface coil may be used to be bound to an object to be scanned by the imaging device.

In some embodiments, the method may further include one or more of the following operations: obtaining scanning information relating to the object, the scanning information including a body length of the object and a scanning region of the object, the surface coil being configured to be bound to the scanning region of the object; determining an estimated target position of the scanning table based on the scanning information, the body length of the object, and/or a predetermined body proportions model; and operating the scanning table to move to the estimated target position.

In some embodiments, the method may further include one or more of the following operations: adjusting the scanning table from the estimated target position to the target position for scanning the object.

In another aspect of the present disclosure, a system for positioning a scanning table is provided. The system may include at least one storage device, and at least one processor in communication with the storage device. The at least one storage device may store a set of instructions. When executing the set of instructions, the at least one processor may be configured to cause the system to: obtain a body length of an object; and/or determine the number of table positions for scanning the object based on a length of each scanning region of the scanning table, an initial length of an overlapping region of the scanning table at two adjacent table positions, and/or the body length of the object.

In some embodiments, the at least one processor may be further configured to cause the system to: determine an effective length of the overlapping region of the scanning table at two adjacent table positions based on the number of the table positions and the body length of the object; and/or adjust the overlapping region of the scanning table at two adjacent table positions based on the effective length of the overlapping region.

In some embodiments, the at least one processor may be further configured to cause the system to: obtain positioning information of the object on the scanning table; determine a scanning direction for scanning the object based on the positioning information; determine a scanning region of the object corresponding to each table position based on the scanning direction, the number of the table positions, and/or a first predetermined relationship between a plurality of scanning regions of one or more objects and a plurality of corresponding table positions; and/or set a scanning protocol at each table position based on the scanning region of the object corresponding to the each table position.

In some embodiments, the predetermined relationship between a plurality of scanning region of one or more objects and a plurality of corresponding table positions may be denoted by a first lookup chart.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
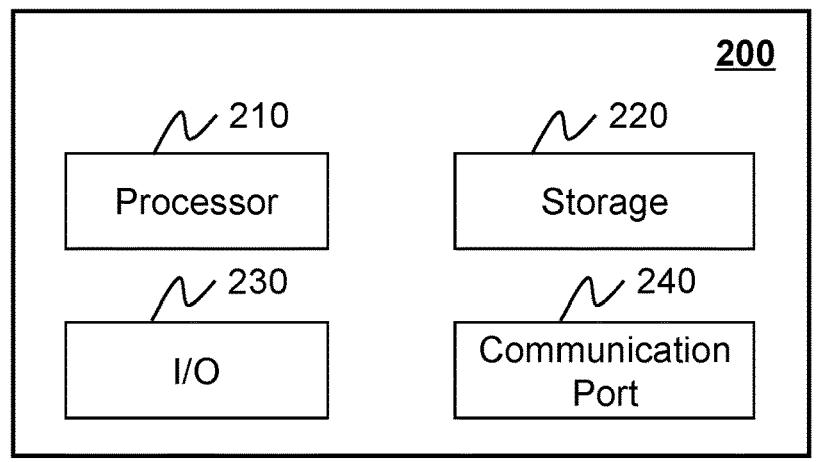
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure provides a method for determining a target position of a scanning table of an imaging system. The imaging system may include but not limited to a computed tomography (CT) system, a positron emission tomography (PET) system, a single photon emission computed tomography (SPECT) system, a magnetic resonance imaging (MRI) system, an emission computed tomography (ECT) system, an ultrasonic imaging (UI) system, or the like, or any combination thereof (e.g., a PET-CT system, a PET-MRI system). A scanning calibration sequence may be obtained. A sensitivity distribution of a surface coil may be determined based on the scanning calibration sequence. A center position of the surface coil may be determined based on the sensitivity distribution. A target position of the scanning table may be determined based on the center position of the surface coil. The target table position of the scanning table may correspond to the center position of the surface coil when the center position of the surface coil is located coincident with a scanning center of an imaging device of the imaging system.

Figure 1:
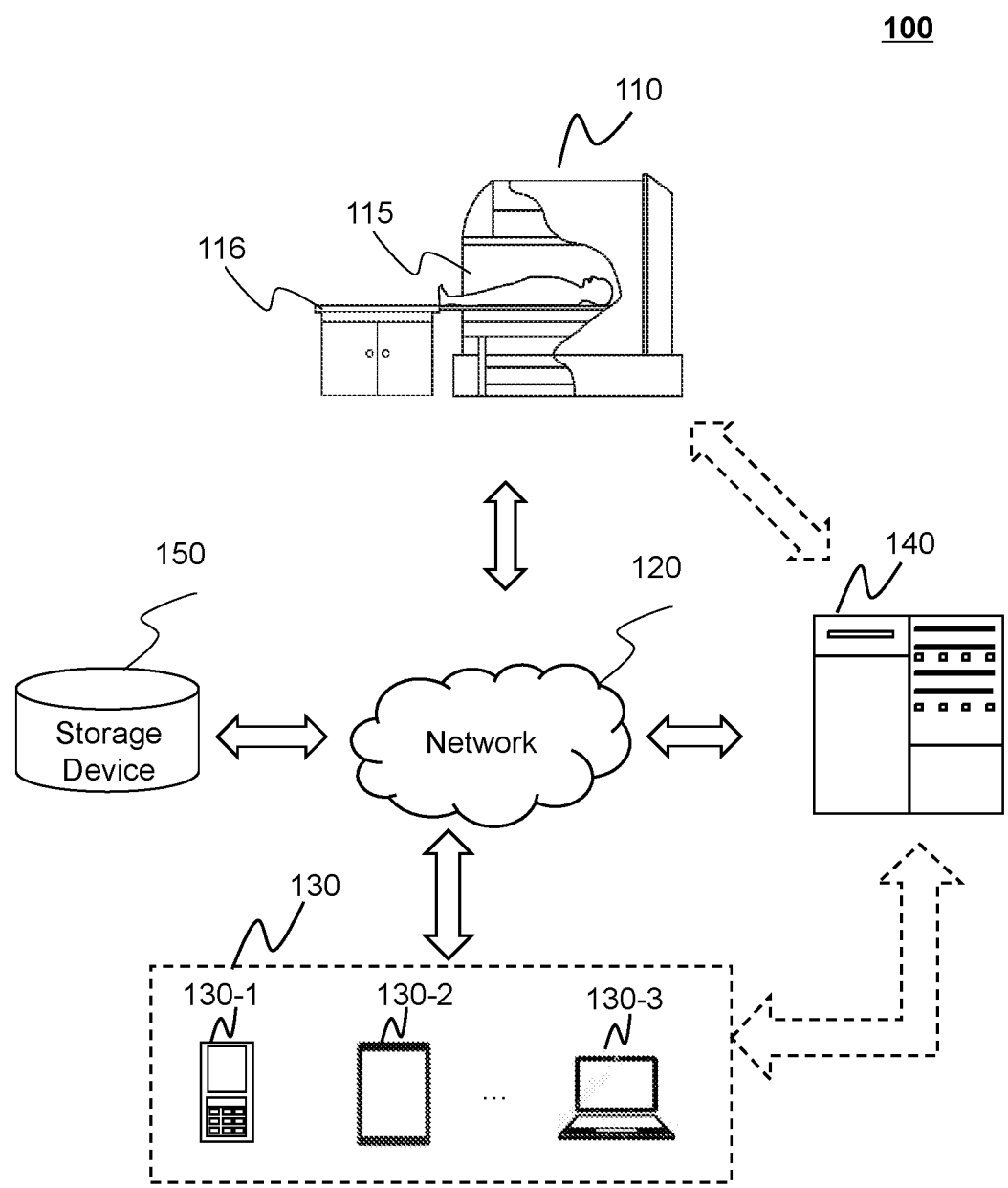
FIG. 1 is a schematic diagram illustrating an exemplary imaging system according to some embodiments of the present disclosure.

FIG. 1 is a schematic diagram illustrating an exemplary imaging system according to some embodiments of the present disclosure. As illustrated, the imaging system 100 may include an imaging device 110, a network 120, one or more terminals 130, a processing device 140, and a storage device 150. The components in the imaging system 100 may be connected in one or more of various ways. Merely by way of example, as illustrated in FIG. 1, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120.

The imaging device 110 may scan an object located within its detection region 115 and generate a plurality of data relating to the object. The object may be placed on the scanning table 116 for scanning. In the present disclosure, "object" and "subject" are used interchangeably. The object may include a biological object (e.g., a human, an animal), a non-biological object (e.g., a phantom), etc. In some embodiments, the imaging device 110 may be a closed-bore scanner or an open-bore scanner.

In some embodiments, the imaging device 110 may include a magnet assembly (e.g., a superconducting magnet), a gradient coil assembly, and/or a radiofrequency (RF) coil assembly (not shown in FIG. 1). The magnet assembly may generate a first magnetic field (also referred to as a main magnetic field) for polarizing the object to be scanned. The magnet assembly may include a permanent magnet, a superconducting magnet, a resistive electromagnet, etc. In some embodiments, the magnet assembly may further include shim coils for maintaining the homogeneity of the main magnetic field.

The gradient coil assembly may generate a second magnetic field (also referred to as a gradient magnetic field). The gradient coil assembly may be designed for either a closed-bore scanner or an open-bore scanner. The gradient coil assembly may include X-gradient coils, Y-gradient coils, and Z-gradient coils. The gradient coil assembly may generate one or more magnetic field gradient pulses to the main magnetic field in the X direction (Gx), the Y direction (Gy), and the Z direction (Gz) to encode the spatial information of the object. In some embodiments, the X direction may be designated as a frequency encoding direction, and the Y direction may be designated as a phase encoding direction. In some embodiments, Gx may be used for frequency encoding or signal readout, generally referred to as the frequency encoding gradient or the readout gradient. In some embodiments, Gy may be used for phase encoding, generally referred to as the phase encoding gradient. In some embodiments, Gz may be used for slice selection for obtaining 2D k-space data. In some embodiments, Gz may be used for phase encoding for obtaining 3D k-space data.

The RF coil assembly may include a plurality of RF coils. The RF coils may include one or more RF transmit coils and/or one or more RF receiver coils. The RF transmit coil(s) may transmit RF pulses to the object. Under the coordinated action of the main magnetic field, the gradient magnetic field, and the RF pulses, MR signals relating to the object may be generated. The RF receiver coil(s) may receive MR signals from the object. In some embodiments, one or more RF coils may both transmit RF pulses and receive MR signals at different times. In some embodiments, the function, size, type, geometry, position, amount, and/or magnitude of the RF coil(s) may be determined or changed according to one or more specific conditions. For example, according to the difference in function and size, the RF coil(s) may be classified as volume coil(s) and local coil(s). In some embodiments, an RF receiver coil may correspond to a channel. The RF receiver coil(s) may receive a plurality of channels of MR signals from the object. The received MR signal(s) may be sent to the processing device 140 directly or via the network 120 for image reconstruction and/or image processing.

In some embodiments, the imaging device 110 may include a supporting assembly (e.g., a gantry), a detector assembly, a detection region 115, a scanning table 116, an electronics module, and a cooling assembly. The detector assembly may detect radiation events (e.g., gamma photons) emitted from the detection region 115. In some embodiments, the detector assembly may include one or more detectors. The detectors may be implemented in any suitable manner, for example, a ring, an arc, a rectangle, an array, or the like, or any combination thereof. In some embodiments, a detector may include one or more crystal elements and/or one or more photomultipliers (e.g., silicon photomultiplier (SiPM), photomultiplier tube (PMT)). The electronics module may collect electrical signals generated based on the radiation events detected by the detector assembly. The cooling assembly may cool the detector assembly.

The network 120 may include any suitable network that can facilitate the exchange of information and/or data for the imaging system 100. In some embodiments, one or more components in the imaging system 100 (e.g., the imaging device 110, the terminal 130, the processing device 140, or the storage device 150) may communicate information and/or data with one or more other components of the imaging system 100 via the network 120. For example, the processing device 140 may obtain signals (e.g., MR signals, PET signals, CT signals) from the imaging device 110 via the network 120. As another example, the processing device 140 may obtain user instructions from the terminal 130 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smartwatch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include Google Glasses™, an Oculus Rift™, a Hololens™ a Gear VR™, etc. In some embodiments, the terminal(s) 130 may remotely operate the imaging device 110. In some embodiments, the terminal(s) 130 may operate the imaging device 110 via a wireless connection. In some embodiments, the terminal(s) 130 may receive information and/or instructions inputted by a user, and send the received information and/or instructions to the imaging device 110 or to the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted.

The processing device 140 may process data and/or information obtained from the imaging device 110, the terminal(s) 130, and/or the storage device 150. For example, the processing device 140 may obtain a scanning calibration sequence, for example, from the storage device 150. In some embodiments, the processing device 140 may determine a sensitivity distribution of a surface coil based on the scanning calibration sequence. In some embodiments, the processing device 140 may determine a center position of the surface coil based on the sensitivity distribution. In some embodiments, the processing device 140 may determine a target position (also referred to as a target table position) of the scanning table 116 based on the center position of the surface coil. In some embodiments, the processing device 140 may be a single server, or a server group. The server group may be centralized, or distributed. In some embodiments, the processing device 140 may be local or remote. For example, the processing device 140 may access information and/or data stored in the imaging device 110, the terminal(s) 130, and/or the storage device 150 via the network 120. As another example, the processing device 140 may be directly connected to the imaging device 110, the terminal(s) 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data or information obtained from the imaging device 110. For example, the processing device 140 may obtain a scanning calibration sequence, for example, from the storage device 150. In some embodiments, the storage device 150 may store data obtained from the terminal(s) 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the imaging system 100 (e.g., the processing device 140, the terminal(s) 130, etc.). In some embodiments, one or more components in the imaging system 100 may access the data or instructions stored in the storage device 150 via the network 120. In some embodiments, the storage device 150 may be directly connected to or communicate with one or more components in the imaging system 100 (e.g., the processing device 140, the terminal(s) 130, etc.). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data and/or image obtained from the imaging device 110, the terminal(s) 130, the storage device 150, and/or any other component in the imaging system 100. Specifically, the processor 210 may obtain a scanning calibration sequence, for example, from the storage device 150. In some embodiments, the processor 210 may further determine a sensitivity distribution of a surface coil based on the scanning calibration sequence. In some embodiments, the processor 210 may perform instructions to control the imaging device 110. For example, the processor 210 may determine an estimated target position of the scanning table 116, and operate the scanning table 116 to move to the estimated target position. As another example, the processor 210 may adjust the scanning table 116 from the estimated target position to a target position for scanning the object. In some embodiments, the processor 210 may perform instructions obtained from the terminal(s) 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal 130, the storage device 150, or any other component of the imaging system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program (e.g., in the form of computer-executable instruction) for the processing device 140 for obtaining a scanning calibration sequence to determine a sensitivity distribution of a surface coil. As another example, the storage 220 may store a program (e.g., in the form of computer-executable instruction) for determining a center position of the surface coil based on the sensitivity distribution. As a further example, the storage 220 may store a program (e.g., in the form of computer-executable instruction) for determining a target position of the scanning table 116 based on the center position of the surface coil.

The I/O 230 may input or output signals, data, and/or information. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the imaging device 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
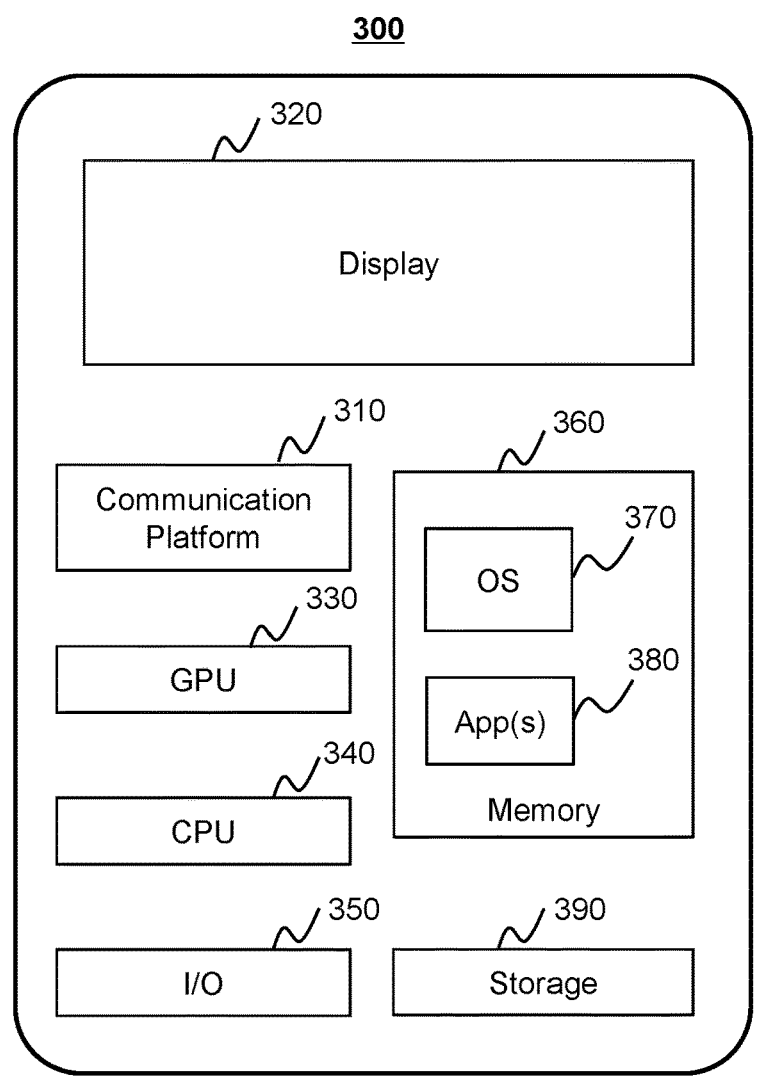
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to determine an unwrapped phase image as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 4:
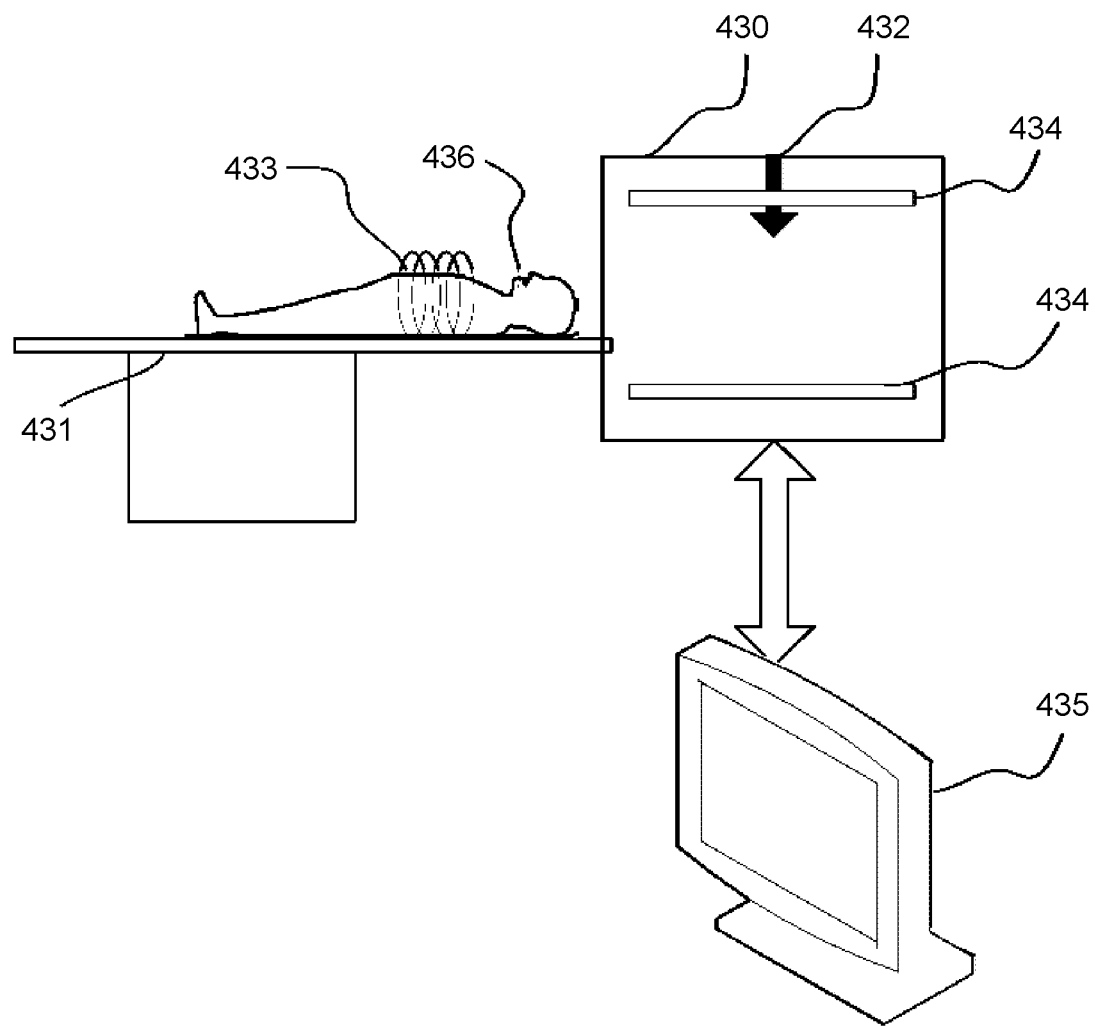
FIG. 4 is a schematic diagram illustrating an exemplary scanning system according to some embodiments of the present disclosure.

FIG. 4 is a schematic diagram illustrating an exemplary scanning system according to some embodiments of the present disclosure. As illustrated, the scanning system 400 may include a gantry bore 430, a scanning table 431, a scanning element 432, a surface coil (or local coil) 433, a volume coil 434, and a positioning sub-system 435.

The gantry bore 430 may form a space for accommodating an object 436 (e.g., a patient). The gantry bore 430 may support the scanning element 432 and the volume coil 434. In some embodiments, the gantry bore 430 may be a hollow bore. The object placed on the scanning table 431 may be moved into the gantry bore 430 for scanning. In some embodiments, a detection region of the gantry bore 430 may cover the entire object, so that a whole body scanning image of the object 436 may be obtained by only one scan. Alternatively, the detection region of the gantry bore 430 may cover only a part of the object 436. The scanning image of different parts of the object 436 may be obtained by two or more scans. The scanning table 431 may be capable of moving in and/or out the gantry bore 430 along an axial direction of the gantry bore 430. In some embodiments, the movement direction of the scanning table 431 may not need to be changed in the operation for determining one or more target positions of the scanning table 431.

The scanning table 431 may support the object 436, and may move towards the gantry bore 430 in the operation for determining one or more target positions of the scanning table 431. The object 436 may be placed on the scanning table 431 for scanning. In some embodiments, the scanning table 431 may change the movement direction while moving.

In some embodiments, the scanning system 400 may be a hybrid magnetic resonance (MR) and positron emission tomography (PET) imaging system, which comprises a PET scanning system having a PET scanning field of view and an MR scanning system having an MR scanning field of view. In some embodiments, the MR scanning field of view overlapped at least a portion of the PET scanning field of view. In some embodiments, the scanning table 431 may have front and back ends, and the scanning table 431 can be translated from a first position outside the respective scanning fields to a second position. In some embodiments, a hybrid MR-PET scan may be performed by a multi-station stop and shoot scheme wherein the scan data may be collected at intervals while the scanning table 431 is moved in discrete steps. In some embodiments, the scanning may be performed when the patient table is stationary between the discrete steps. In some embodiments, each discrete step taken may have any desired distance, so that a region scanned on the object (e.g., a patient) can be adjacent to and/or overlapping with another region scanned on the object. In some embodiments, a desired distance may be determined based on one or more of the following operations: determining one or more parameters associated with the object (e.g., a patient) for scanning; determining the number (or count) of table positions for scanning the object based on a length of each scanning region of the scanning table, an initial length of an overlapping region of the scanning table at two adjacent table positions, and the parameters. Meanwhile, the desired distance of the scanning table 431 movement between different table positions can also be determined. In some embodiments, the parameters may include a body length of the object.

The scanning element 432 may scan a scanning region of the object 436. In some embodiments, the scanning element 432 may be mounted on the gantry bore 430. The scanning center of the scanning system 400 may be indicated by the center position of the scanning element 432. The scanning region of the object 436 may include one or more portions of the object, for example, a head, a foot, a chest, an abdomen, an organ (e.g., a brain, a lung, a liver, a stomach, a rib, a vertebra, etc.), or the like, or any combination thereof. The scanning element 432 may include a positron emission source, an X-ray emission source, a magnetic field, or the like, or any combination thereof. In some embodiments, the location of the scanning element 432 may be fixed, for example, the scanning element 432 may be mounted at the top center of the gantry bore 430. In some embodiments, the location of the scanning element 432 may be changeable. For example, the scanning element 432 may be mounted outside the gantry bore 430 and change positions according to the needs of a scanning process.

The surface coil 433 may be bound to the scanning region of the object 436. The surface coil 433 may be a radio frequency (RF) coil configured to receive RF signals associated with the scanning region of the object 436. In some embodiments, the surface coil 433 may include a coil with flexible cable, a circularly polarized coil, a phased array coil, an X-nuclei coil, an arterial spin labeling (ASL) coil, a multichannel array coil, or the like, or any combination thereof.

The volume coil 434 may be mounted on the gantry bore 430. The volume coil 434 may provide a relatively high RF magnetic field homogeneity and/or a relatively high signal to noise ratio (SNR). The volume coil 434 may be a circularly polarized volume coil, a transmit-receive volume coil, a volume coil with active detuning, a volume array coil, an X-nuclei volume coil, or the like.

The positioning sub-system 435 may be configured to determine a target position of the scanning table 431. For example, the positioning sub-system 435 may determine a sensitivity distribution of the surface coil 433 based on a scanning calibration sequence. The scanning calibration sequence may be stored in the positioning sub-system 435 in advance, or may be input by a user (e.g., a doctor). The positioning sub-system 435 may determine a center position of the surface coil based on the sensitivity distribution. The center position may be a position at which the surface coil 433 has an effective maximum sensitivity. The effective maximum sensitivity may have a value corresponding to a highest point of the sensitivity distribution of the surface coil 433. The positioning sub-system 435 may determine a target position of the scanning table 431 based on the center position of the surface coil 433. The target position of the scanning table 431 may correspond to the center position of the surface coil 433 when the center position of the surface coil 433 is located coincident with a scanning center of the scanning system 400. The scanning center may coincide with a center position, for example, of the scanning element 432.

Figure 5:
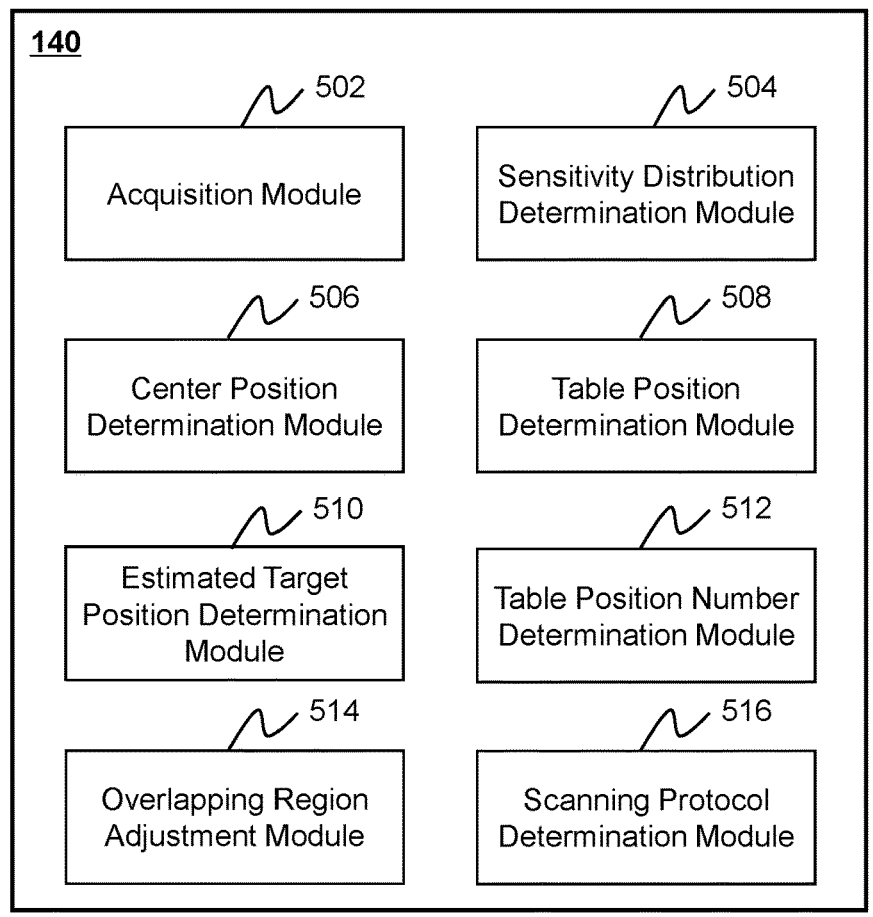
FIG. 5 is a block diagram illustrating an exemplary processing device according to some embodiments of the present disclosure.

FIG. 5 is a block diagram illustrating an exemplary processing device according to some embodiments of the present disclosure. As illustrated in FIG. 5, the processing device 140 may include an acquisition module 502, a sensitivity distribution determination module 504, a center position determination module 506, a table position determination module 508, an estimated table position determination module 510, a table position number determination module 512, an overlapping region adjustment module 514, and a scanning protocol determination module 516.

The acquisition module 502 may acquire data relating to a scan of an object. The data may include a scanning calibration sequence. The scanning calibration sequence may include a radio frequency pulse sequence and/or a gradient pulse sequence. The radio frequency pulse sequence may be used to perform a radio frequency excitation on the scanning region of an object (e.g., the patient) to generate a corresponding magnetic resonance signal. The gradient pulse sequence may include an x-gradient pulse signal, a y-gradient pulse signal, a z-gradient pulse signal, or the like, or any combination thereof. In some embodiments, the acquisition module 502 may acquire scanning information relating to the object, for example, a body length (also referred to as a height) of the object, a scanning region of the object, positioning information of the object, or the like, or any combination thereof. The positioning information may include information about a position (e.g., a posture, an orientation, etc.) of the object relative to the imaging device, such as a head first-prone position, a head first-supine position, a head first-decubitus right position, a head first-decubitus left position, a feet first-decubitus right position, a feet first-decubitus left position, a feet first-prone position, a feet first-supine position, etc. In some embodiments, the acquisition module 502 may acquire the data relating to the scanning of the object from the storage 150, an external data source, and/or any other device that is capable of providing scanning data.

The sensitivity distribution determination module 504 may determine a sensitivity distribution of the surface coil based on the scanning calibration sequence. The sensitivity distribution may represent a relationship between an effective sensitivity value and a position of the surface coil. In some embodiments, the surface coil may include one or more coil units. The sensitivity distribution determination module 504 may determine a first signal intensity distribution of each coil unit of the surface coil and a second signal intensity distribution of a volume coil based on the scanning calibration sequence. The first signal intensity distribution may be generated based on a first signal. The first signal may be a magnetic resonance signal in a one-dimensional (1D) encoding direction collected by each coil unit. The first signal may be generated by scanning the object based on the scanning calibration sequence. The second signal intensity distribution may be generated based on a second signal. The second signal may be a magnetic resonance signal in the one-dimensional (1D) encoding direction collected by the volume coil. The second signal may be generated by scanning an object based on the scanning calibration sequence. In some embodiments, the one-dimensional (1D) encoding direction may be the main magnetic field direction along the imaging device. The sensitivity distribution determination module 504 may fuse the first signal intensity distribution of the each coil unit and the second signal intensity distribution to obtain the sensitivity distribution of the each coil unit of the surface coil, for example, a value of the first signal intensity distribution for each coil unit may be divided by a corresponding value of the second signal distribution of the volume coil to obtain the sensitivity distribution of the each coil unit.

The center position determination module 506 may determine a center position of the surface coil based on the sensitivity distribution. The center position may be a position at which the surface coil has a maximum sensitivity value. In some embodiments, the surface coil may include only one coil unit, the center position determination module 506 may identify a first location of the one coil unit corresponding to an effective maximum sensitivity based on the sensitivity distribution of the one coil unit. The effective maximum sensitivity may be determined based on the sensitivity distribution of the one coil unit (i.e., the surface coil). The position corresponding to the effective maximum sensitivity of the sensitivity distribution may be determined as the first location. The center position determination module 506 may designate the first location as the center position of the surface. In some embodiments, the surface coil may include at least two coil units. The center position determination module 506 may determine one or more effective units capable of receiving signals from the at least two coil units. A first location of each effective unit corresponding to an effective maximum sensitivity may be determined based on the sensitivity distribution of the each effective unit. The first location may be designated as the center position of the each effective unit. The center position determination module 506 may determine an average position of the center position(s) of the one or more effective units, for example, an arithmetic average position, a geometric average position, a mean square, a harmonic average position, a weighted average position, or the like. The center position determination module 506 may determine the average position as the center position of the surface coil. In some embodiments, the center position determination module 506 may determine whether a distance between the center positions of two adjacent effective units satisfies a threshold. The threshold may relate to a physical distance set in a clinical examination protocol (also referred to as a scanning protocol). In some embodiments, the threshold may be stored in a document recording information relating to coil characteristics and positioning of the coil(s) (e.g., coil unit(s), surface coil, volume coil, or the like). The center position determination module 506 may compare the distance between the center positions of each two adjacent effective units with the threshold. In response to a determination that the distance between the center positions of two adjacent effective units satisfies the threshold, the center position determination module 506 may determine the average position of the center positions of the two adjacent effective units as the center position of the surface coil. In response to a determination that the distance between the center positions of two adjacent effective units dissatisfies the threshold, the center position determination module 506 may take the threshold as a reference to adjust the center position of the two adjacent effective units causing the distance to satisfy the threshold. The center position determination module 506 may determine the average position of the adjusted center positions of the two adjacent effective units as the center position of the surface coil.

The table position determination module 508 may determine a target position of the scanning table based on the center position of the surface coil. The target table position of the scanning table may correspond to the center position of the surface coil when the center position of the surface coil is located coincident with a scanning center of the imaging device. In some embodiments, the scanning center of the imaging device may be fixed. The table position determination module 508 may determine a position of the scanning table at which the center position of the surface coil is located coincident with the scanning center. The table position determination module 508 may determine a position of the scanning table as the target position of the scanning table 433.

The estimated table position determination module 510 may determine an estimated table position. The estimated table position of the scanning table may be an intermediate table position of the scanning table at which the surface coil is close to the scanning center of the imaging device (i.e., the estimated target position of the scanning table may be close to the target position of the scanning table). The estimated table position determination module 510 may determine the estimated table position based on the scanning information, the body length of the object, and/or a predetermined body proportions model. The predetermined body proportions model may be a statistical model of one or more parts of one or more human bodies. The estimated table position determination module 510 may operate the scanning table to move to the estimated target table position.

Figure 14:
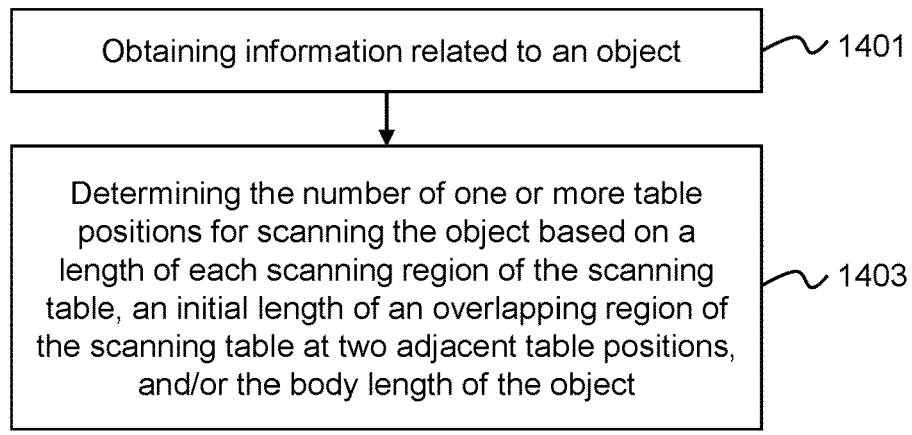
FIG. 14 is a flowchart illustrating an exemplary process for determining the number of one or more table positions for scanning an object according to some embodiments of the present disclosure.

The table position number determination module 512 may determine the number of one or more table positions (or bed positions) for scanning the object. The table position number determination module 512 may determine the number based on a length of each scanning region of the scanning table, an initial length of an overlapping region of the scanning table at two adjacent table positions, and/or the body length of the object. The table position number determination module 512 may determine the number according to Equation (2) as illustrated in FIG. 14.

Figure 15:
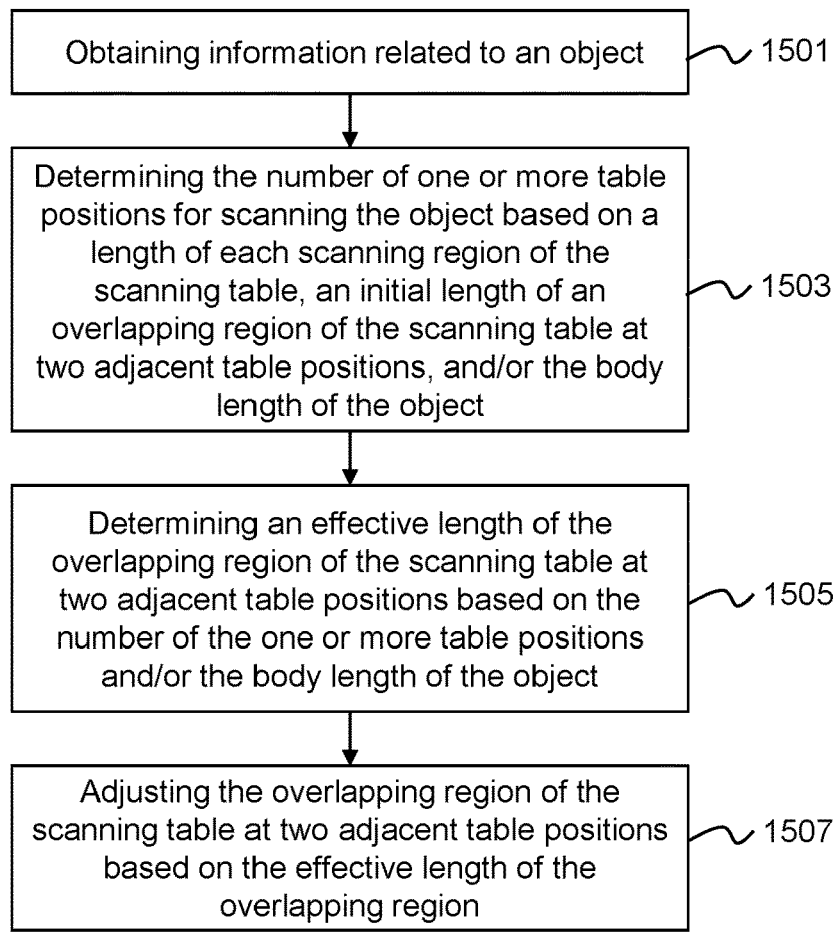
FIG. 15 is a flowchart illustrating an exemplary process for determining the number of one or more table positions for scanning an object according to some embodiments of the present disclosure.

The overlapping region adjustment module 514 may adjust the overlapping region of the scanning table at two adjacent table positions. In some embodiments, the overlapping region adjustment module 514 may determine an estimated length of the overlapping region based on the number of the one or more table positions and/or the body length of the object. The overlapping region adjustment module 514 may determine the estimated length of the overlapping region according to Equation (4) as illustrated in FIG. 15. In some embodiments, the overlapping region adjustment module 514 may determine whether the estimated length is greater than or equal to the initial length of the overlapping region. If the estimated length of the overlapping region is greater than or equal to the initial length of the overlapping region, the overlapping region adjustment module 514 may designate the estimated length of the overlapping region as an effective length of the overlapping region. If the estimated length of the overlapping region is smaller than the initial length of the overlapping region, the overlapping region adjustment module 514) may designate the initial length of the overlapping region as the effective length of the overlapping region. The overlapping region adjustment module 514 may adjust the overlapping region of the scanning table at two adjacent table positions based on the effective length of the overlapping region.

The scanning protocol determination module 516 may set a scanning protocol at each table position based on a scanning region of the object corresponding to the each table position. The scanning region of the object may include one or more portions of the object, for example, a head, a foot, a chest, an abdomen, an organ (e.g., a brain, a lung, a liver, a stomach, a rib, a vertebra, etc.), or the like, or any combination thereof.

In some embodiments, the scanning protocol determination module 516 may determine a scanning direction for scanning the object based on the positioning information of the object. The scanning protocol determination module 516 may determine the scanning protocol for the scanning region of the object corresponding to each table position based on the scanning direction, the number of the one or more table positions, and/or a first predetermined relationship between a plurality of scanning regions of one or more objects and a plurality of corresponding table positions. The scanning protocol determination module 516 may determine the scanning protocol based on the scanning region of the object corresponding to the each table position, and/or a second predetermined relationship between a plurality of scanning regions of one or more objects and a plurality of corresponding scanning protocols. The scanning protocol determination module 516 may set the scanning protocol at the each table position based on the each determined scanning protocol for the scanning region of the object corresponding to the each table position.

It should be noted that the above description of the processing device 140 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the table position determination 508 and the estimated table position determination module 510 may be implemented on a processing unit, hardware or software other than the processing device 140 yet cooperate with the processing device 140 to perform the functions described above.

Figure 6:
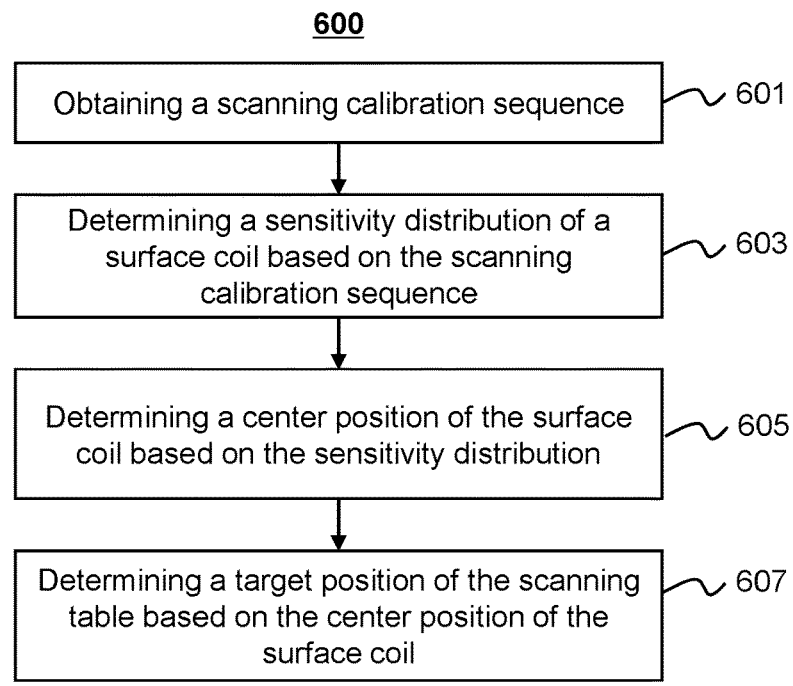
FIG. 6 is a flowchart illustrating an exemplary process for determining a target position of a scanning table according to some embodiments of the present disclosure.

FIG. 6 is a flowchart illustrating an exemplary process for determining a target position of a scanning table according to some embodiments of the present disclosure. In some embodiments, one or more operations of process 600 may be implemented in the imaging system 100 illustrated in FIG. 1 or the imaging system 400 illustrated in FIG. 4. For example, the process 600 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 600 may be implemented on the imaging device of the imaging system 100 or the imaging system 400. The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 601, the processing device 140 (e.g., the acquisition module 502) may obtain a scanning calibration sequence. In some embodiments, the scanning calibration sequence may include a radio frequency pulse sequence and/or a gradient pulse sequence. The radio frequency pulse sequence may be used to perform a radio frequency excitation on the scanning region of an object (e.g., the patient) to generate corresponding magnetic resonance signal(s). The gradient pulse sequence may include an x-gradient pulse signal (also referred to as a gradient pulse signal on the gradient axis of the layer selection direction), a y-gradient pulse signal (also referred to as a gradient pulse signal on the gradient axis of the phase encoding direction), a z-gradient pulse signal (also referred to as a gradient pulse signal on the gradient axis of the readout direction), or the like, or any combination thereof. The gradient pulse sequence may be used to locate the spatial localization code of the scanning region of the object.

The scanning calibration sequence may be acquired from the storage 150 or an external data source. In some embodiments, the scanning calibration sequence may be loaded to the processing device 140 by a user, for example, a doctor, so that the acquisition module 502 may receive the scanning calibration sequence and transfer the scanning calibration sequence to other component(s) of the processing device 140 for subsequent operations.

In 603, the processing device 140 (e.g., the sensitivity distribution determination module 504) may determine a sensitivity distribution of a surface coil (e.g., the surface coil 433) based on the scanning calibration sequence. In some embodiments, the sensitivity distribution may represent a relationship between an effective sensitivity value and a position of the surface coil.

The effective sensitivity value may increase as the distance between the position of the surface coil and the scanning center decreases, and vice versa. For example, if the surface coil approaches the scanning center, the effective sensitivity value may increase. The sensitivity distribution may be expressed in various forms, for example, a curve, a table, a chart, or the like, or any combination thereof. For any position of the surface coil, there may be a corresponding effective sensitivity value. More descriptions of the determination of the sensitivity distribution of the surface coil may be found elsewhere in the present disclosure (e.g., FIG. 7 and the descriptions thereof).

In 605, the processing device 140 (e.g., the center position determination module 506) may determine a center position of the surface coil based on the sensitivity distribution.

In some embodiments, the surface coil may include one or more coil units. The sensitivity distribution of a coil unit may reflect an ability of the coil unit for receiving signals. The ability for receiving signals may relate to the position of the coil unit. The smaller the distance between the center position of the coil unit and the scanning center of the imaging device, the stronger the ability of the coil unit for receiving signals (i.e., the higher the sensitivity of the coil unit). Conversely, the larger the distance between the center position of the coil unit and the scanning center of the imaging device, the weaker the ability of the coil unit for receiving signals (i.e., the lower the sensitivity of the coil unit). Therefore, the center position of each coil unit of the surface coil may be determined based on the relationship between the position and the sensitivity of the coil unit, and/or the sensitivity distribution of the coil unit. Therefore, the center position of the surface coil may be determined based on the center positions of the coil unit(s). More descriptions regarding the determination of the center position of the surface coil may be found elsewhere in the present disclosure (e.g., FIGS. 8-10 and the descriptions thereof).

In 607, the processing device 140 (e.g., the table position determination module 508) may determine a target position of the scanning table based on the center position of the surface coil. The target position of the scanning table may correspond to the center position of the surface coil when the center position of the surface coil is located coincident with a scanning center of the imaging device.

In some embodiment, in an imaging system (e.g., the imaging system 100), the scanning center of the imaging device may be fixed during a scanning process. The scanning center may be preset in the imaging system 100 in advance, or may be manually adjusted according to different application scenarios by the user of the imaging system 100 (e.g., a doctor).

In some embodiments, the table position determination module 406 may determine a distance between the center position of the surface coil and the scanning center, and a direction from the center position of the surface coil to the scanning center, based on the center position of the surface coil and the position of the scanning center. The surface coil may be moved for the distance along the direction until the center position of the surface coil is located coincident with the scanning center. If the surface coil is located coincident with the scanning center, the position of the scanning table may be determined as the target position of the scanning table.

Merely by way of example, assuming that the surface coil includes two coil units, a first coil unit BAC1 and a second coil unit BAC2, and both of the two coil units are effective units capable of receiving signals, according to the sensitivity distribution of the coil units, the center positions of the first coil unit BAC1 and the second coil unit BAC2 may be determined as −80 and 60 relative to a predetermined reference position (e.g., the scanning center), respectively. In some embodiments, the center position of the surface coil may be determined as −10 by averaging the center positions of the two coil units. If position of the scanning center is 0, the surface coil has to be moved for 10 units of distance in a prescribed direction, so that the center position of the surface coil may be located at the scanning center. If the center position of the surface coil is located at the scanning center, the position of the scanning table may be determined as the target position of the scanning table.

As illustrated above, the center position of the surface coil can be located using the sensitivity distribution of the surface coil, and the target position of the scanning table may be determined based on the center position of the surface coil and the position of the scanning center. Compared with the method for determining the target position of the scanning table using a laser lamp, the operations illustrated in the present disclosure may not need to repeatedly move the scanning table during the positioning process, thereby reducing the complexity of the operations. The target position of the scanning table 433 can be determined quickly and accurately. Moreover, operations illustrated in the present disclosure may not need to use a laser lamp, thereby preventing the damage to the eyes of the object caused by the laser.

It should be noted that the above description of the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 7:
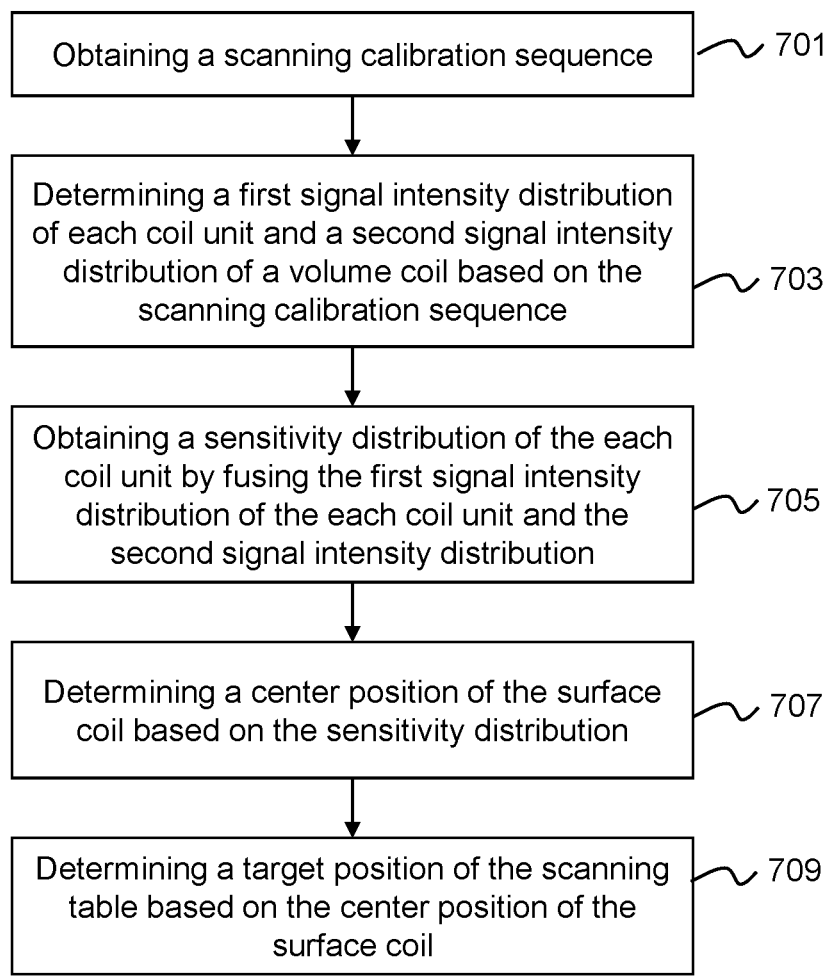
FIG. 7 is a flowchart illustrating an exemplary process for determining a target position of a scanning table according to some embodiments of the present disclosure.

FIG. 7 is a flowchart illustrating an exemplary process for determining a target position of a scanning table according to some embodiments of the present disclosure. In some embodiments, one or more operations of process 700 may be implemented in the imaging system 100 illustrated in FIG. 1 or the imaging system 400 illustrated in FIG. 4. For example, the process 700 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 700 may be implemented on the imaging device of the imaging system 100 or the imaging system 400. The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting. In some embodiments, operation 603 illustrated in FIG. 6 may be performed according to operations 703 and 705 of the process 700.

Referring to FIG. 7, some operations, for example, 701, 707, and 709, may be the same as or similar to those in 601, 605, and 609 of FIG. 6, respectively, the descriptions of which are not repeated here.

In 703, the processing device 140 (e.g., the sensitivity distribution determination module 504) may determine a first signal intensity distribution of each coil unit of the at least one coil unit and a second signal intensity distribution of a volume coil of the imaging device based on the scanning calibration sequence.

In some embodiments, the surface coil may include one or more coil units. The volume coil may be mounted in the scanning cavity (or detection region) of the imaging device (e.g., the gantry bore). In some embodiments, the position of the volume coil in the gantry bore may be fixed.

In some embodiments, the first signal intensity distribution may be generated based on a first signal. The first signal may be a magnetic resonance signal in a one-dimensional (1D) encoding direction collected by each coil unit. The first signal may be generated by scanning the object based on the scanning calibration sequence. The second signal intensity distribution may be generated based on a second signal. The second signal may be a magnetic resonance signal in the one-dimensional (1D) encoding direction collected by the volume coil. The second signal may be generated by scanning the object based on the scanning calibration sequence. In some embodiments, the one-dimensional (1D) encoding direction may be the main magnetic field direction along the imaging device.

In some embodiments, the first signal(s) collected by the coil unit(s) may be subjected to one or more operations (e.g., channel merging, image processing, or the like, or any combination thereof) to obtain a first signal intensity distribution curve for each coil unit. A first signal intensity distribution curve may reflect the first signal intensity distribution of a corresponding coil unit. Similarly, the second signal collected by the volume coil may be subjected to one or more operations (e.g., channel merging, image processing, or the like) to obtain a second signal intensity distribution curve for the volume coil. The second signal intensity distribution curve may reflect the second signal intensity distribution of the volume coil.

In 705, the processing device 140 (e.g., the sensitivity distribution determination module 504) may determine the sensitivity distribution of the each coil unit by fusing the first signal intensity distribution of the each coil unit and the second signal intensity distribution.

Because the contents of hydrogen atoms in different tissue regions of different human bodies are different, it could be understood that the density of hydrogen atoms varies widely in different tissue regions. Therefore, based on the principle of magnetic resonance, in a magnetic resonance system, the signal intensities of the magnetic resonance signals generated by different tissue regions may be different. Therefore, the first signal intensity distribution of the each coil unit and the second signal intensity distribution of the volume coil may be affected by the influences of the tissue structure of the object and an imaging contrast on the characteristics of the coil unit(s) and/or the volume coil. The imaging contrast may refer to a brightness of the signal. The imaging contrast may be mainly affected by one or more parameters including for example, a relaxation time of a scanning tissue, a repetition time of the scanning calibration sequence, an echo time of the scanning calibration sequence, or the like. That is, the first signal intensity distribution of a coil unit may not reflect the sensitivity distribution of the coil unit accurately. Therefore, the effects of the tissue structure of the object and/or the imaging contrast may need to be removed to obtain an accurate sensitivity distribution of the each coil unit.

As illustrated above, the sensitivity of the volume coil and/or the coil unit(s) may be affected by the tissue structure of the object and/or the contrast. If the second signal intensity distribution of the volume coil is used as a reference, then the first signal intensity distribution of the each coil unit may be fused with the second signal intensity distribution of the volume coil to obtain a relatively accurate sensitivity distribution for the each coil unit.

In some embodiments, the fusing operation may refer to that each value of the first signal intensity distribution for each coil unit is divided by a corresponding value of the second signal distribution of the volume coil. Thereby, the influences of the tissue structure of the object or the contrast on the characteristics of the coil unit(s) and/or the volume coil may be removed or reduced. In some embodiments, the sensitivity distribution of the each coil unit may be obtained by normalizing the first signal intensity using the second signal intensity of the volume coil.

In some embodiments, a clinical examination protocol (also referred to as a scanning protocol) may be set before scanning. According to the clinical examination protocol, different detection parts (also referred to as scanning regions) of the object may be detected by different surface coils or different coil units. That is, different detection parts of the object may use different numbers of coil units, and the coil units used for different detection parts may be different. Therefore, one or more processes may be performed to determine the center position of the surface coil based on the situations of the coil units set in the clinical examination protocols and the sensitivity distribution of the surface coil. In some embodiments, the surface coil may include one or more coil units. In some embodiments, the process for determining the center position of the surface coil including one coil unit may be different from that of the surface coil including two or more coil units. For example, if the surface coil includes only one coil unit, the process for determining the center position of the surface coil may be found in FIG. 8 and the descriptions thereof. If the surface coil includes at least two coil units, the process for determining the center position of the surface coil may be found in FIGS. 9-10 and the descriptions thereof.

It should be noted that the above description of the process 700 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 703 may be divided into two or more operations (e.g., the first signal intensity distribution of each coil unit may be determined in a first operation, while the second signal intensity distribution of the volume coil may be determined in a second operation).

Figure 8:
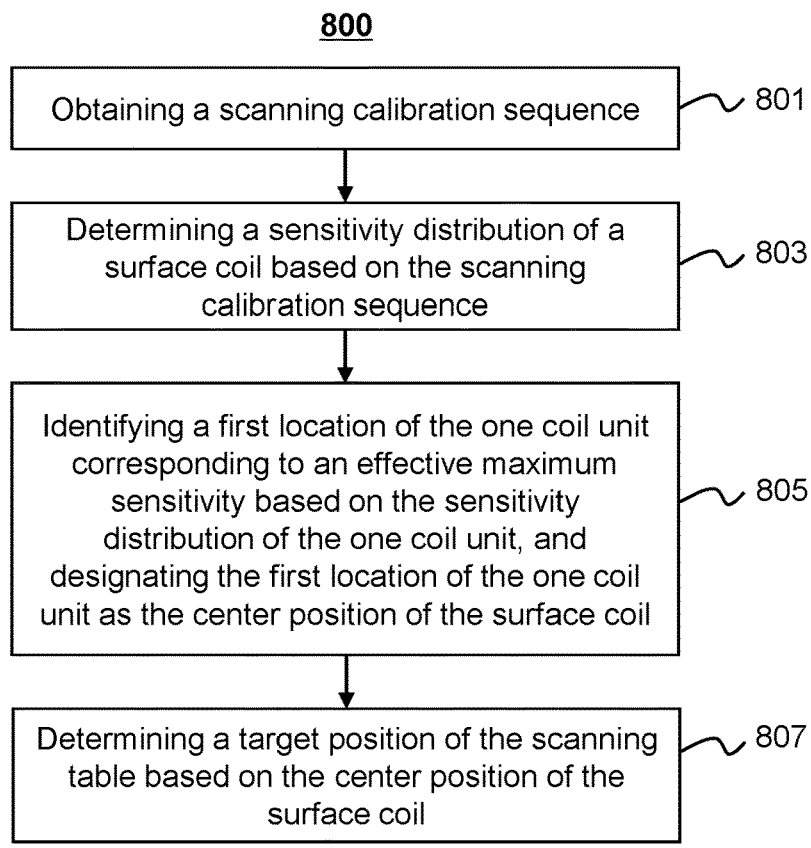
FIG. 8 is a flowchart illustrating an exemplary process for determining a target position of a scanning table according to some embodiments of the present disclosure.

FIG. 8 is a flowchart illustrating an exemplary process for determining a target position of a scanning table according to some embodiments of the present disclosure. In some embodiments, one or more operations of process 800 may be implemented in the imaging system 100 illustrated in FIG. 1 or the imaging system 400 illustrated in FIG. 4. For example, the process 800 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 800 may be implemented on the imaging device of the imaging system 100 or the imaging system 400. The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting.

Referring to FIG. 8, some operations, for example, 801, 803, and 807, may be the same as or similar to those in 601, 603, and 607 of FIG. 6, respectively, the descriptions of which are not repeated here. In some embodiments, the surface coil may include only one coil unit, and accordingly, the operation for determining the center position of the surface coil may be illustrated in 805.

In 805, the processing device 140 (e.g., the center position determination module 506) may identify a first location of the one coil unit corresponding to an effective maximum sensitivity based on the sensitivity distribution of the one coil unit, and designate the first location of the one coil unit as the center position of the surface coil.

In some embodiments, the sensitivity distribution of the one coil unit may reflect the ability of the one coil unit for receiving signals, and the ability of the one coil unit for receiving signals may have a certain relationship with the position of the one coil unit. The smaller the distance between the center position of the one coil unit and the scanning center of the imaging device, the greater the effective sensitivity value. It may be indicated that the maximum of the effective sensitivity value (i.e., the effective maximum sensitivity) corresponds to the center position of the one coil unit (i.e., the center position of the surface coil).

In some embodiments, the effective maximum sensitivity may be determined based on the sensitivity distribution of the one coil unit (i.e., the surface coil). Assuming that the sensitivity distribution of the one coil unit (i.e., the surface coil) is denoted by a curve, the sensitivity value corresponding to the highest point of the curve may be the maximum value (i.e., the effective maximum sensitivity). The curve may denote the relationship between the sensitivity value and the position of the one coil unit (i.e., the surface coil). Therefore, the position corresponding to the effective maximum sensitivity may be determined as the first location, and the first location may be designated as the center position of the surface coil.

It should be noted that the above description of the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 803 may be performed according to operations 703 and 703 of the process 700.

Figure 9:
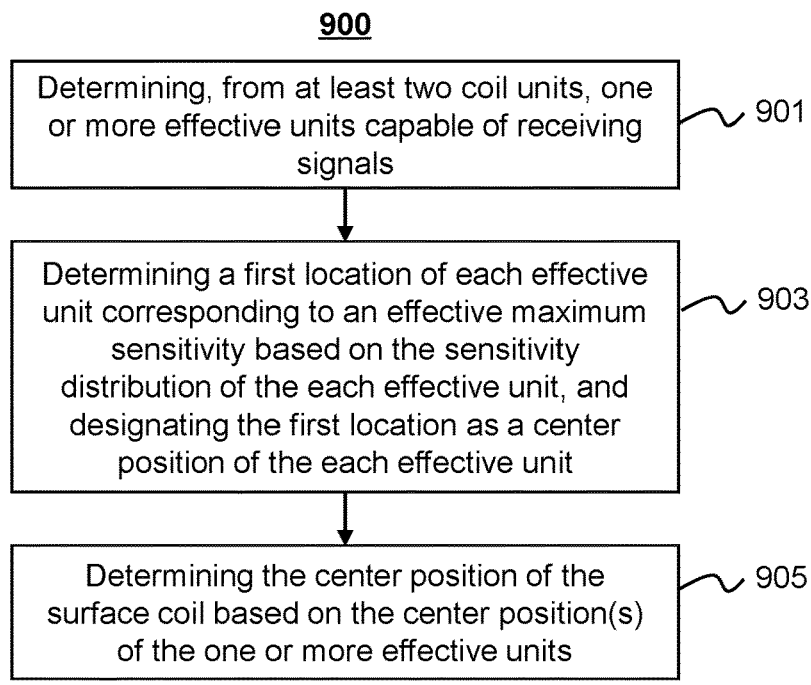
FIG. 9 is a flowchart illustrating an exemplary process for determining a center position of a surface coil according to some embodiments of the present disclosure.

FIG. 9 is a flowchart illustrating an exemplary process for determining a center position of a surface coil according to some embodiments of the present disclosure. In some embodiments, one or more operations of process 900 may be implemented in the imaging system 100 illustrated in FIG. 1 or the imaging system 400 illustrated in FIG. 4. For example, the process 900 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 900 may be implemented on the imaging device of the imaging system 100 or the imaging system 400. The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting. In some embodiments, operation 605 illustrated in FIG. 6 may be performed according to the process 900. In some embodiments, the surface coil may include at least two coil units, and accordingly, the operation for determining the center position of the surface coil may be illustrated in 901-905.

In 901, the processing device 140 (e.g., the center position determination module 506) may determine one or more effective units capable of receiving signals from the at least two coil units.

In some embodiments, if a coil unit of the surface coil is damaged, for example, the metal wire of the coil unit is broken, failing to form a complete loop, the coil unit may be determined as ineffective. In some embodiments, the effective units may be determined based on the types and/or numbers of signals obtained by applying a magnetic field to the surface coil. For example, if the surface coil includes two coil units, and two different signals are received, then the surface coil may have two effective units. As another example, if only one signal is received, then the surface coil may have only one effective unit.

In 903, the processing device 140 (e.g., the center position determination module 506) may determine a first location of each effective unit corresponding to an effective maximum sensitivity based on the sensitivity distribution of the each effective unit, and may designate the first location as a center position of the each effective unit.

In some embodiments, as described in FIG. 8, the sensitivity distribution of each effective unit may reflect the ability of the each effective unit for receiving signals, and the ability of the each effective unit for receiving signals may have a certain relationship with the position of the effective unit. The smaller the distance between the center position of the each effective unit and the scanning center of the imaging device, the greater the effective sensitivity value. It may be indicated that the maximum of the effective sensitivity value (e.g., the effective maximum sensitivity) corresponds to the center position of the each effective unit.

In some embodiments, the effective maximum sensitivity may be determined based on the sensitivity distribution of the each effective unit. Assuming that the sensitivity distribution of the each effective unit is denoted by a curve, the sensitivity value corresponding to the highest point of the curve may be the maximum value (i.e., the effective maximum sensitivity). The curve may denote the relationship between the sensitivity value and the position of the each effective unit. The position corresponding to effective maximum sensitivity may be determined as the first location, and the first location may be designated as the center position of the each effective unit.

In some embodiments, the center position of each effective unit may be located within a detection range (or the range of the scanning region of the imaging device) covered by a current position of the scanning table. The detection range at one position of the scanning table may be a preset range of the imaging device. In some embodiments, the detection range may be 40 cm-50 cm.

In 905, the processing device 140 (e.g., the center position determination module 506) may determine the center position of the surface coil based on the center position(s) of the one or more effective units.

In some embodiments, the center position(s) of the one or more effective units may be processed based on a preset rule. The preset rule may refer to a processing principle of combining the center position(s) of the one or more effective units into one position. In some embodiments, according to an exemplary preset rule, an average position of the center position(s) of the one or more effective units may be determined, and the average position may be designated as the center position of the surface coil.

In some embodiments, the average position of the center position(s) of the one or more effective units may be an average value of the center position(s). The average value may be an arithmetic average value, a geometric average value, a mean square value, a harmonic average value, a weighted average value, or the like. In some embodiments, the average position of the center position(s) may be an average value of the root square(s) of the center position(s).

Merely by way of example, assuming that the surface coil includes two coil units (e.g., unit 1 and unit 2), and both the two coil units are effective units capable of receiving signals, according to the sensitivity distribution of the two coil units, the center positions of unit 1 and unit 2 may be determined as −50 and 30, respectively. Therefore, the center position of the surface coil may be determined as −10 by averaging the center positions of the two coil units (i.e., (−50+30)/2=−10).

It should be noted that the center position of the surface coil may be a position determined by combining the center position(s) of the effective unit(s). Each of the center position(s) of the effective unit(s) may be within a detection range covered by a current position of the scanning table. Therefore, the center position of the surface coil may also be within the detection range covered by the current position of the scanning table.

In some embodiments, the preset rule may be set as inherent information of the imaging system 100 (or the imaging system 400). In some embodiments, according to different scenarios, the preset rule may be a default setting set by a manufacturer or a user (e.g., a doctor). It should be noted that the preset rule illustrated above is merely provided for the purposes of illustration, and not intended to limit the scope of the present disclosure.

It should be noted that the above description of the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, the number of the effective units may affect the subsequent operations. For example, if the surface coil includes two coil units, and one coil unit is ineffective (i.e., the surface coil may include only one effective unit), then the center position of the surface coil may be determined according to operation 805 of the process 800. As another example, if the number of the effective units is equal to or larger than 2, then the center position of the surface coil may be determined according to the process 1000 in FIG. 10.

Figure 10:
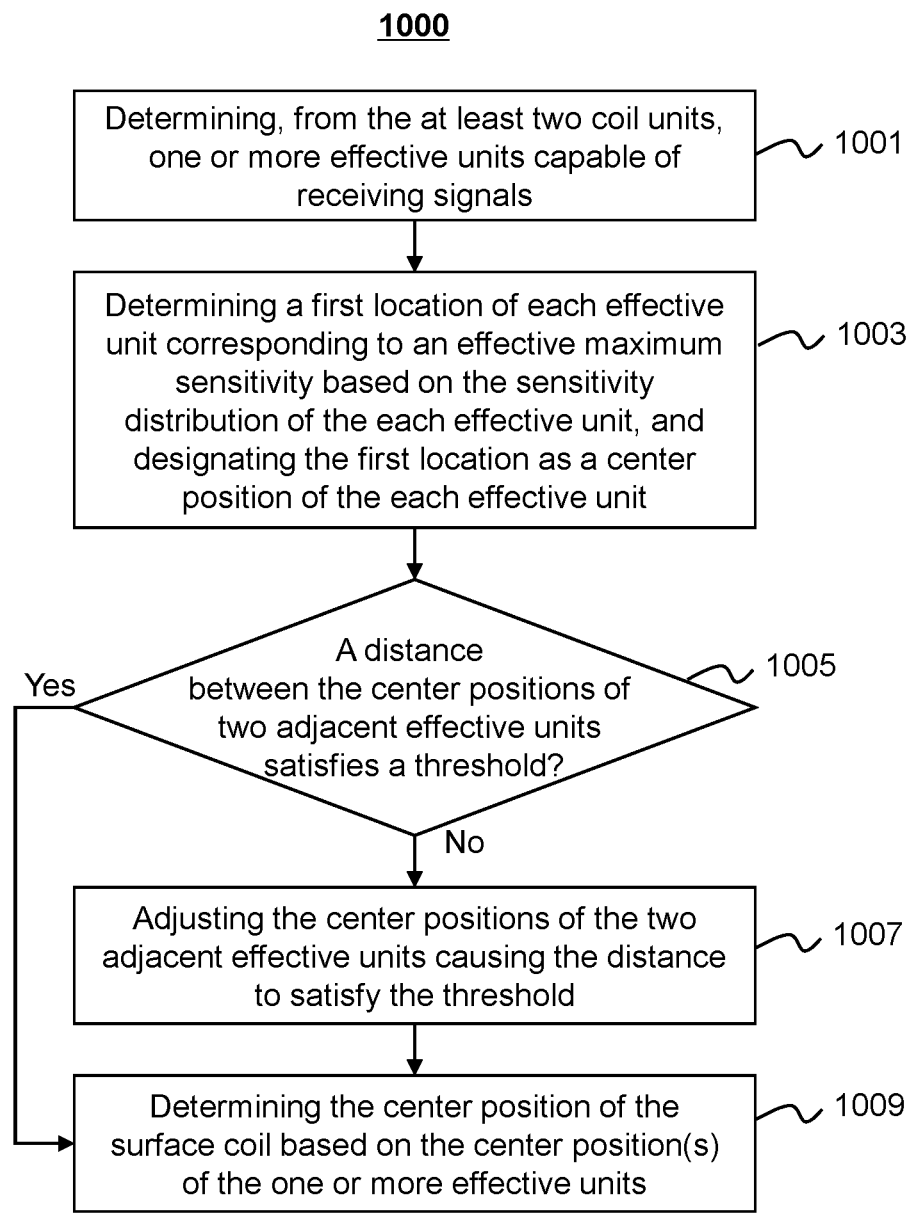
FIG. 10 is a flowchart illustrating an exemplary process for determining a target position of a scanning table according to some embodiments of the present disclosure.

FIG. 10 is a flowchart illustrating an exemplary process for determining a target position of a scanning table according to some embodiments of the present disclosure. In some embodiments, one or more operations of process 1000 may be implemented in the imaging system 100 illustrated in FIG. 1 or the imaging system 400 illustrated in FIG. 4. For example, the process 1000 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1000 may be implemented on the imaging device of the imaging system 100 or the imaging system 400. The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting. In some embodiments, operation 605 illustrated in FIG. 6 may be performed according to the process 1000.

Referring to FIG. 10, some operations, for example, 1001, 1003, and 1009, may be the same as or similar to those in 901, 903, and 905 of FIG. 9, respectively, the descriptions of which are not repeated here.

In 1005, the processing device 140 (e.g., the center position determination module 506) may determine whether a distance between the center positions of two adjacent effective units satisfies a threshold. The threshold may relate to a physical distance set in a clinical examination protocol (also referred to as a scanning protocol). In some embodiments, the processing device 140 may compare the distance between the center positions of each two adjacent effective units with the threshold. In response to a determination that the distance dissatisfies the threshold, the process 1000 may proceed to 1007. In response to a determination that the distance satisfies the threshold, the process 1000 may proceed to 1009.

In some embodiments, the threshold may be a preset value stored in the imaging system 100 (e.g., the storage device 150 and/or the storage 220) or the imaging system 400 in advance. In some embodiments, the threshold may be stored in a computer-readable file recording information relating to coil characteristics and positioning of the coil(s) (e.g., coil unit(s), surface coil, volume coil, or the like). In some embodiments, the processing device 140 (e.g., the center position determination module 506) may obtain the threshold by accessing the storage device 150 and/or the storage 220.

In 1007, the processing device 140 (e.g., the center position determination module 506) may adjust the center positions of the two adjacent effective units causing the distance to satisfy the threshold.

In some embodiments, the center position determination module 506 may take the threshold as a reference and adjust the center positions of the two adjacent effective units. In some embodiments, the center position determination module 506 may reduce the distance between the center positions of the two adjacent effective units, until the distance between the center positions of the two adjacent effective units satisfies the threshold.

Merely by way of example, assuming that the threshold is 20 mm, an effective unit A is adjacent to an effective unit B, and the center position a of the effective unit A is 22 mm away from the center position b of the effective unit B, the center position determination module 506 may reduce the distance between the center positions of the two effective units to make the center positions get close to each other. If the distance between the center positions of the two effective units reaches 20 mm, the center position determination module 506 may stop the adjustment of the center positions. Correspondingly, an adjusted center position a' of the effective unit A and an adjusted center position b' of the effective unit B may be recorded, respectively. The adjusted center positions a' and b' may be further used to determine the average center position of the surface coil.

If the distance between the (adjusted) center positions of each two adjacent effective units satisfies the threshold, a second location may be determined based on the (adjusted) center positions of the one or more effective units. In some embodiments, the (adjusted) center positions of the one or more effective units may be processed based on the preset rule (see FIG. 9) to obtain the second location. For example, the second location may be an average position of the (adjusted) center positions of the one or more effective units. Then the second location may be designated as the center position of the surface coil.

It should be noted that the above description of the process 1000 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1007 may be omitted.

Figure 11:
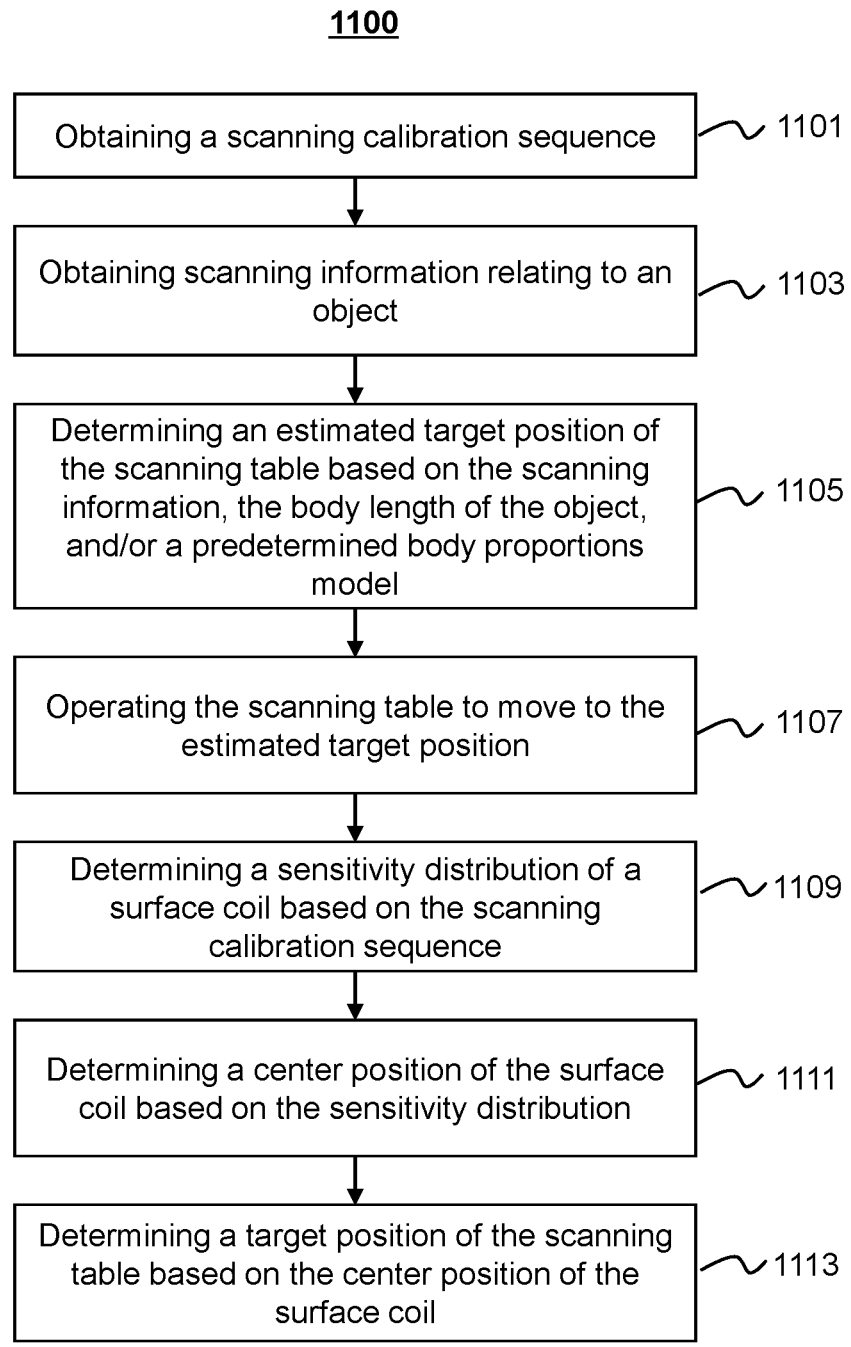
FIG. 11 is a flowchart illustrating an exemplary process for determining a target position of a scanning table according to some embodiments of the present disclosure.

FIG. 11 is a flowchart illustrating an exemplary process for determining a target position of a scanning table according to some embodiments of the present disclosure. In some embodiments, one or more operations of process 1100 may be implemented in the imaging system 100 illustrated in FIG. 1 or the imaging system 400 illustrated in FIG. 4. For example, the process 1100 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1100 may be implemented on the imaging device of the imaging system 100 or the imaging system 400. The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

Referring to FIG. 11, some operations, for example, 1101, 1109, 1111, and 1113, may be the same as or similar to those in 601, 603, 605 and 607 of FIG. 6, respectively, the descriptions of which are not repeated here.

In 1103, the processing device 140 (e.g., the acquisition module 502) may obtain scanning information relating to the object.

In some embodiments, the scanning information may include but not limited to a body length (also referred to as a height) of the object, a scanning region of the object, positioning information of the object, or the like, or any combination thereof. In some embodiments, the surface coil may be bound to the scanning region of the object.

In some embodiments, the object may be a patient. In some embodiments, the scanning information may further include the name, age, gender, nationality, race, height, and/or weight of the object, or the like, or any combination thereof. The scanning region may refer to a region of the object to be scanned by the imaging device. The scanning region may include one or more portions of the object, for example, a head, a foot, a chest, an abdomen, an organ (e.g., a brain, a lung, a liver, a stomach, a rib, a vertebra, etc.), or the like, or any combination thereof. The positioning information may include information about a position (e.g., a posture, an orientation, etc.) of the object relative to the imaging device. For example, the positioning information may include one or more coordinates, angles, etc. that can represent the position of the object.

In some embodiments, the position of the object relative to the imaging device can include and/or be one or more known positions, such as a head first-prone position, a head first-supine position, a head first-decubitus right position, a head first-decubitus left position, a feet first-decubitus right position, a feet first-decubitus left position, a feet first-prone position, a feet first-supine position, etc. A head first-prone position may refer to a position in which the object's head is positioned towards a front of the imaging device and the object's face is positioned in a downward (gravity) direction. A head first-supine position may refer to a position in which the object's head is positioned towards the front of the imaging device and the object's face is positioned in an upward direction. A head first-decubitus right position may refer to a position in which the object's head is positioned towards the front of the imaging device and the object's right side is positioned in a downward direction. A head first-decubitus left position may refer to a position in which the object's head is positioned towards the front of the imaging device and the object's left side is positioned in a downward direction. A feet first-decubitus right position may refer to a position in which the object's feet is positioned towards the front of the imaging device and the object's right side is positioned in a downward direction. A feet first-decubitus left position may refer to a position in which the object's feet is positioned towards the front of the imaging device and the object's left side is positioned in a downward direction. A feet first-prone position may refer to a position in which the object's feet is positioned towards the front of the imaging device and the object's face is positioned in a downward (gravity) direction. A feet first-supine position may refer to a position in which the object's feet is positioned towards the front of the imaging device and the subject's face is positioned in an upward direction. The front of the imaging device may refer to a front side of the imaging device in which the scanning table may enter the gantry bore.

In 1105, the processing device 140 (e.g., the estimated target position determination module 510) may determine an estimated target position of the scanning table based on the scanning information, the body length of the object, and/or a predetermined body proportions model.

In some embodiments, the estimated target position of the scanning table may be an intermediate table position of the scanning table at which the surface coil is close to the scanning center of the imaging device (i.e., the estimated target position of the scanning table may be close to the target position of the scanning table). In some embodiments, the predetermined body proportions model may be a statistical model of one or more parts of one or more human bodies. The proportions of different parts of human bodies of different genders and/or different races may be different. The estimated target position corresponding to the object may be determined based on the corresponding predetermined body proportions model and the scanning information (e.g., the body length, gender, or nationality of the object, or the like). More descriptions of the predetermined body proportions model may be found elsewhere in the present disclosure (e.g., FIG. 16 and the descriptions thereof).

In 1107, the processing device 140 (e.g., the estimated target position determination module 510) may operate the scanning table to move to the estimated target position.

In some embodiments, the estimated target position determination module 510 may determine a distance between the center position of the surface coil and the estimated target position, and/or a direction from the center position of the surface coil to the estimated target position. The surface coil may be moved for the distance along the direction, so that the surface coil can be located coincident with the estimated target position.

It should be noted that the above description of the process 1100 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1101 may be performed after any one of operations 1103-1107.

As illustrated above, process(es) for determining a target position of a scanning table are described in FIGS. 6-11. According to the operations mentioned above, an exemplary process for determining a target position of a scanning table is described below. Assuming that a lower limb of the object 436 is to be scanned, a surface coil may be bound to the lower limb of the object 436. Assuming that the length of the lower limb is 1 m, and the detection range is 40 cm-50 cm, two table positions may be required for scanning the lower limb. Therefore, two target positions of the scanning table may need to be determined. The two target positions of the scanning table may be determined in sequence. Each of the two target positions of the scanning table may be determined according to the process(es) of FIGS. 6-11. The processing device 140 may obtain scanning information relating to the object 436 (see operation 1103). The processing device 140 may determine an estimated target position of the scanning table based on the scanning information, the body length of the object, and/or a predetermined body proportions model (see operation 1105). The processing device 140 may obtain a scanning calibration sequence (see operation 1101). Assuming that the surface coil bound to the lower limb of the object 436 includes a first effective unit BAC1 and a second effective unit BAC2, the processing device 140 may determine, based on the scanning calibration sequence, a first signal intensity distribution (see FIG. 12) of the first effective unit BAC1, and a first signal intensity distribution (see FIG. 12) of the second effective unit BAC2. The processing device 140 may determine a second signal intensity distribution (see FIG. 12) of a volume coil. The processing device 140 may fuse the first signal intensity distribution of the first effective unit BAC1 and the second signal intensity distribution of the volume coil and obtain a sensitivity distribution (see FIG. 13) of the first effective unit BAC1. For example, the processing device 140 may divide each value of the first signal intensity distribution of the first effective unit BAC1 by a corresponding value of the second signal intensity distribution of the volume coil. The processing device 140 may fuse the first signal intensity distribution of the second effective unit BAC2 and the second signal intensity distribution of the volume coil and obtain a sensitivity distribution (see FIG. 13) of the second effective unit BAC2. For example, the processing device 140 may divide each value of the first signal intensity distribution of the second effective unit BAC2 by a corresponding value of the second signal intensity distribution of the volume coil. The processing device 140 may determine a first location (e.g., $d_1$) of the first effective unit BAC1 corresponding to an effective maximum sensitivity of the sensitivity distribution of the first effective unit BAC1. The processing device 140 may determine a first location (e.g., $d_2$) of the second effective unit BAC2 corresponding to an effective maximum sensitivity of the sensitivity distribution of the second effective unit BAC2. Assuming that the distance $L_1$ between $d_1$ and $d_2$ satisfies the threshold, the processing device 140 may determine an average value D of $d_1$ and $d_2$, and designate the average value D as the center position of the surface coil. Then the processing device 140 may cause the scanning table to move to the scanning center of the imaging device. If the center position of the surface coil is located coincident with the scanning center of the imaging device, the processing device 140 may designate the corresponding position of the scanning table as a target position of the scanning table.

Figure 12:
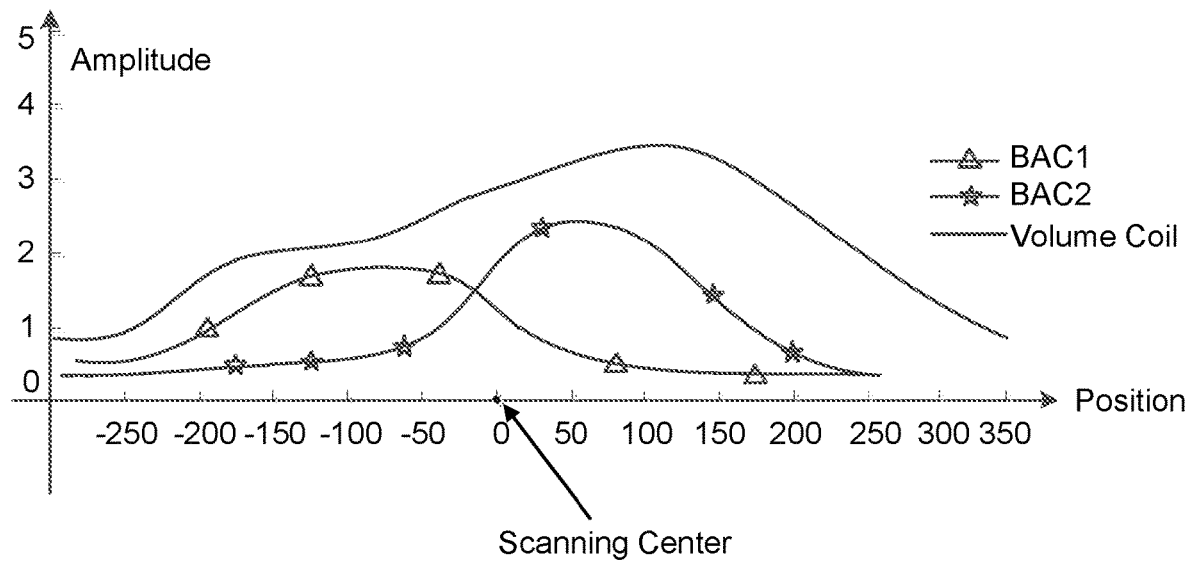
FIG. 12 is a schematic diagram illustrating two exemplary first signal intensity distribution curves of two effective units of a surface coil and an exemplary second signal intensity distribution curve of a volume coil according to some embodiments of the present disclosure.

FIG. 12 is a schematic diagram illustrating two exemplary first signal intensity distribution curves of two effective units (e.g., an effective unit BAC1 and an effective unit BAC2) of a surface coil and an exemplary second signal intensity distribution curve of a volume coil according to some embodiments of the present disclosure. The horizontal axis represents the position of the scanning region of the imaging device, and the vertical axis represents the amplitude of the signal intensity. As illustrated in FIG. 12, the scanning center is set as a reference position (i.e., the abscissa of the scanning center is 0), and the abscissas of other positions have coordinates relative to the scanning center. A coordinate point with a negative abscissa value may indicate that the position corresponding to the coordinate point locates between the scanning center and the inlet of the gantry bore of the imaging device. A coordinate point with a positive abscissa value may indicate that the position corresponding to the coordinate point locates between the scanning center and an interior of the gantry bore of the imaging device. The curves (i.e., the two first signal intensity distribution curves of the effective units BAC1 and BAC2 of the surface coil and the second signal intensity distribution curve of the volume coil) may be generated based on a plurality of position-amplitude data sets. In some embodiments, the curves may fluctuate around the horizontal axis, indicating that the signal intensity received by the coil units and/or the volume coil may change with the position. As shown in FIG. 12, each curve has a highest point, indicating that the signal received at the corresponding position may have the largest intensity.

Figure 13:
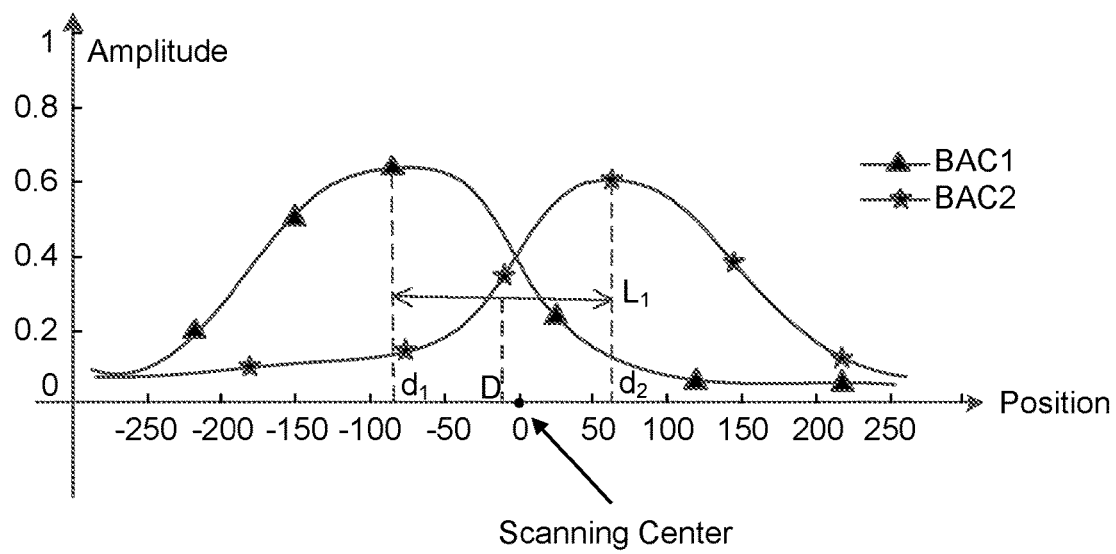
FIG. 13 is a schematic diagram illustrating two exemplary sensitivity distribution curves of two effective units according to some embodiments of the present disclosure.

FIG. 13 is a schematic diagram illustrating two exemplary sensitivity distribution curves of two effective units (e.g., an effective unit BAC1 and an effective unit BAC2) according to some embodiments of the present disclosure. The horizontal axis represents the position of the scanning region of the imaging device, and the vertical axis represents the amplitude of the effective sensitivity value. The amplitude of the effective sensitivity value shown in FIG. 13 is normalized. Similar to FIG. 12, the scanning center is set as a reference position (i.e., the abscissa of the scanning center is 0), and the abscissas of other positions have coordinates relative to the scanning center. A coordinate point with a negative abscissa value may indicate that the position corresponding to the coordinate point locates between the scanning center and the inlet of the gantry bore of the imaging device. A coordinate point with a positive abscissa value may indicate that the position corresponding to the coordinate point locates between the scanning center and an interior of the gantry bore of the imaging device. As shown in FIG. 13, the position corresponding to the maximum amplitude of the sensitivity distribution curve of the effective unit BAC1 is $d_1$, and the position corresponding to the maximum amplitude of the sensitivity distribution curve of the effective unit BAC2 is $d_2$. In some embodiments, assuming that the distance $L_1$ between $d_1$ and $d_2$ satisfies the threshold, an average value D (e.g., an arithmetic average value, a geometric average value, a mean square, a harmonic average value, a weighted average value, or the like) of $d_1$ and $d_2$ may be determined. In some embodiments, the average position of the center position(s) may be an average value of the root squares of $d_1$ and $d_2$. The average value D of $d_1$ and $d_2$ may be designated as the center position of the surface coil.

FIG. 14 is a flowchart illustrating an exemplary process for determining the number of one or more table positions for scanning an object according to some embodiments of the present disclosure. In some embodiments, one or more operations of process 1400 may be implemented in the imaging system 100 illustrated in FIG. 1 or the imaging system 400 illustrated in FIG. 4. For example, the process 1400 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1400 may be implemented on the imaging device of the imaging system 100 or the imaging system 400. The operations of the illustrated process presented below are intended to be illustrative. In some embodiments, the process 1400 may be accomplished with one or more additional operations not described, and/or without one or more of the operations discussed. Additionally, the order in which the operations of the process 1400 as illustrated in FIG. 14 and described below is not intended to be limiting.

In 1401, the processing device 140 (e.g., the acquisition module 502) may obtain information related to an object (e.g., registration information of the object).

In some embodiment, if a scan (e.g., a PET-CT scanning, a PET-MRI scanning) is required for the object, information related to the object may be registered in the imaging system 100 (or the imaging system 400) in advance. The information may include but not limited to parameters related to the object, scanning region of the object, positioning information of the object, or the like, or any combination thereof. The parameters related to the object may include name, age, gender, nationality, race, height, weight, or the like, or any combination thereof. The height of the object may also referred to as the body length of the object.

In some embodiments, the information may be stored in, for example, the storage 150. In some embodiments, the processing device 140 may obtain the information related to the object by accessing the storage 150 directly or via the network 120.

In 1403, the processing device 140 (e.g., the table position number determination module 512) may determine the number of one or more table positions for scanning the object. In some embodiments, the processing device 140 may determine the number of table positions based on a length of each scanning region of the scanning table, an initial length of an overlapping region of the scanning table at two adjacent table positions, and/or the body length of the object.

In some embodiments, the detection range of an imaging device may be fixed or limited (e.g., depending on the size of the gantry bore, the sizes and/or positions of the coils, etc.). Correspondingly, a scanning region (or detection range) of the scanning table at each table position may be fixed or limited. In some embodiments, during a single scanning, the detection range of the imaging device may not cover a target portion of the object to be scanned (e.g., the whole body of the object). Therefore, one or more scans may be required for detecting the target portion of the object to be scanned. In each scan of the one or more scans, the scanning table may need to be moved to a corresponding (target) table position. For example, assuming that the detection range of the imaging device is 30 cm, and the scanning region of the object is 50 cm, two scans may be required. If the scanning table locates at a first table position, a portion of the scanning region of the object may be scanned. If the scanning table is moved to a second position, another portion of the scanning region of the object may be scanned. Therefore, one or more table positions may need to be determined. At two adjacent table positions, the scanning region of the scanning table may be overlapped. On the one hand, the processing device 140 may determine the number of the table position(s) for scanning the object. One the other hand, the processing device 140 may determine each target position of the table position(s). More descriptions of the determination of the each target position may be found elsewhere in the present disclosure (e.g., FIGS. 6-11 and the descriptions thereof).

In some embodiments, to achieve a relatively high image quality and/or stability, there may be an overlapping region of the scanning table at two adjacent table positions. The initial length of an overlapping region of the scanning table at two adjacent table positions may be denoted by, for example, overlap$_{min}$ (e.g., a minimum overlap percentage, also a minimum percentage of the overlapping region in the scanning region of the scanning table).

In some embodiment, the table position number determination module 512 may extract the body length (e.g., the height) of the object from the information and determine the number of the one or more table positions for scanning the object based the height of the object, the length of each scanning region of the scanning table, and the initial length of an overlapping region of the scanning table at two adjacent table positions through mathematical calculation.

In some embodiments, the body length of the object may be obtained before scanning, so that the number of the one or more table positions for scanning the object may be automatically determined and/or planned. Therefore, an operator may not need to manually adjust or set the number of table positions of the scanning table, and the inspection time for scanning the object may be shorten. In some embodiments, a risk of damage caused by one or more radiopharmaceuticals uptaken by the object may be reduced.

In some embodiments, the number of one or more table positions for scanning the object may be determined according to the following operations.

Assuming that the body length of the object is height, the length of each scanning region of the scanning table is length, and the initial length of an overlapping region of the scanning table at two adjacent table positions is overlap$_{min}$, the number of the one or more table positions couchsize may satisfy the following expression:

$$\text{length}*\text{couchsize}-\text{length}*\text{overlap}_{min}(\text{couchsize}-1) \geq \text{height}. \quad (1)$$

Because the number of table position(s) is an integer, the couchsize may be determined according to Equation (2):

$$couchsize = \text{ceil}\left(\frac{\text{height}+\text{length}*overlap_{min}}{\text{length}*(1-overlap_{min})}\right), \quad (2)$$

where the cell function refers to a determination of a minimum integer that is greater than or equal to $$\frac{\text{height}+\text{length}*overlap_{min}}{\text{length}*(1-overlap_{min})}.$$

It should be noted that the above description of the process 1400 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

FIG. 15 is a flowchart illustrating an exemplary process for determining the number of one or more table positions for scanning an object according to some embodiments of the present disclosure. In some embodiments, one or more operations of process 1500 may be implemented in the imaging system 100 illustrated in FIG. 1 or the imaging system 400 illustrated in FIG. 4. For example, the process 1400 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1500 may be implemented on the imaging device of the imaging system 100 or the imaging system 400. The operations of the illustrated process presented below are intended to be illustrative. In some embodiments, the process 1500 may be accomplished with one or more additional operations not described, and/or without one or more of the operations discussed. Additionally, the order in which the operations of the process 1500 as illustrated in FIG. 15 and described below is not intended to be limiting.

Referring to FIG. 15, some operations, for example, 1501 and 1503, may be the same as or similar to those in 1401 and 1403 of FIG. 14, respectively, the descriptions of which is not repeated here.

In 1505, the processing device 140 (e.g., the overlapping region adjustment module 514) may determine an effective length of the overlapping region of the scanning table at two adjacent table positions based on the number of the one or more table positions and/or the body length of the object.

In some embodiments, according to the number of the one or more table positions for scanning the object and/or the initial length of an overlapping region of the scanning table at two adjacent table positions, the portions of the object scanned at the first table position and/or the last table position may be determined. In some embodiments, the portions of the object scanned at the first table position and/or the last table position may not occupy the whole detection range of the imaging device. In some embodiments, in order to avoid the situation that the portions of the object scanned at the first table position and/or the last table position occupy only a relatively small part of the whole detection range of the imaging device (i.e., a relatively large part of empty scanning table or air is scanned at the first table position and/or the last table position), it may be desirable to adjust the length of the overlapping region of the scanning table at two adjacent table positions. More descriptions regarding the determination of the effective length of the overlapping region of the scanning table may be found elsewhere in the present disclosure (e.g., FIG. 18 and the descriptions thereof).

In 1507, the processing device 140 (e.g., the overlapping region adjustment module 514) may adjust the overlapping region of the scanning table at two adjacent table positions based on the effective length of the overlapping region.

In some embodiments, the overlapping region of the scanning table at two adjacent table positions may be adjusted by adjusting the target position(s) of the scanning table. For example, if the overlapping region needs to be increased, one target position of the scanning table may need to be moved to be further away from an adjacent target position of the scanning table, or the two adjacent target positions of the scanning table may be moved away from each other. As another example, if the overlapping region needs to be decreased, one target position of the scanning table may need to be moved to be closer to an adjacent target position of the scanning table, or the two adjacent positions of the scanning table may be moved to be closer to each other.

In some embodiments, the overlapping region of the scanning table at two adjacent table positions may be automatically adjusted based on the effective length of the overlapping region to complete a scanning table positioning process. Therefore, the operator does not need to manually adjust the overlapping region of the scanning table at two adjacent table positions, the automatic planning and/or adjustment of the overlapping region of the scanning table at two adjacent table positions may be realized, and the inspection time may be further shortened.

It should be noted that the scanning table positioning process in the present disclosure may refer to the determining of the number of one or more table positions for scanning the object based on the information including for example, the body length of the object, and the automatic adjustment of the overlapping region of the scanning table at two adjacent table positions based on the effective length of the overlapping region. A scan for the object may be performed after the scanning table positioning process.

It should be noted that the above description of the process 1500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 16:
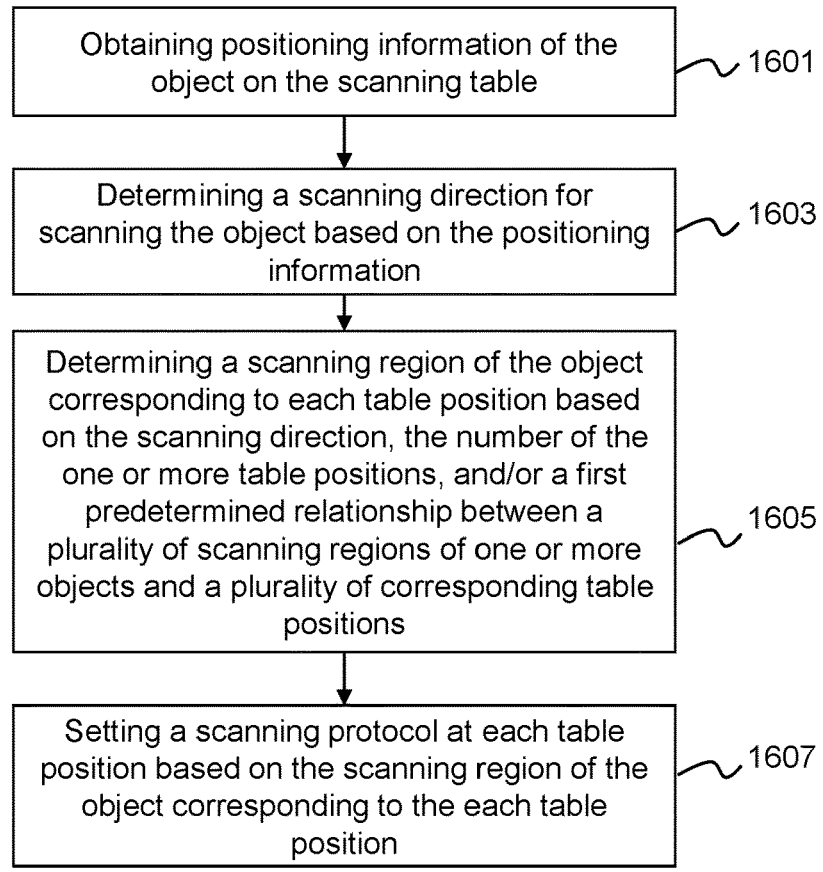
FIG. 16 is a flowchart illustrating an exemplary process for determining the number of one or more table positions for scanning an object according to some embodiments of the present disclosure.

FIG. 16 is a flowchart illustrating an exemplary process for determining the number of one or more table positions for scanning an object according to some embodiments of the present disclosure. In some embodiments, one or more operations of process 1600 may be implemented in the imaging system 100 illustrated in FIG. 1 or the imaging system 400 illustrated in FIG. 4. For example, the process 1600 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1600 may be implemented on the imaging device of the imaging system 100 or the imaging system 400. The operations of the illustrated process presented below are intended to be illustrative. In some embodiments, the process 1600 may be accomplished with one or more additional operations not described, and/or without one or more of the operations discussed. Additionally, the order in which the operations of the process 1600 as illustrated in FIG. 16 and described below is not intended to be limiting.

In 1601, the processing device 140 (e.g., the acquisition module 502) may obtain positioning information of the object on the scanning table. In some embodiments, the positioning information of the object on the scanning table may include and/or be one or more known positions, such as a head first-prone position, a head first-supine position, a head first-decubitus right position, a head first-decubitus left position, a feet first-decubitus right position, a feet first-decubitus left position, a feet first-prone position, a feet first-supine position, etc. More descriptions of the positioning information of the object may be found elsewhere in the present disclosure (e.g., FIG. 11 and the descriptions thereof).

In 1603, the processing device 140 (e.g., the scanning protocol determination module 516) may determine a scanning direction for scanning the object based on the positioning information.

In some embodiments, in order to further improve the scanning efficiency, a scanning direction of a scanning protocol of a scout image of the object (e.g., a portion of the body of the object, the whole body of the object) may be determined based on the positioning information. Thereby, the scanning direction for scanning the object may be determined based on the scanning direction of the scanning protocol of the scout image. In some embodiments, a scan (e.g., PET scanning) of the object may be performed to obtain the scout image of the whole body of the object. If the positioning information of the object is head first-prone position or head first-supine position (i.e., the head is close to the center of the magnet), and the scanning direction of the scanning protocol of the scout image is set from the foot (or feet) to the head of the object, then the scanning table may need to be moved before scanning the scout image. In order to avoid unnecessary table-moving, the scanning direction of the scanning protocol of the scout image may be set from the head to the foot (or feet), and accordingly, the scanning direction for scanning the object may be set from the foot (or feet) to the head. That is, after scanning the scout image (at this time the foot (or feet) is close to the center of the magnet), the object may be directly scanned from the foot (or feet) to the head to realize scanning during the resetting process of the scanning table. Therefore, the time spent for resetting the scanning table may be reasonably utilized, and the scanning efficiency may be improved.

In 1605, the processing device 140 (e.g., the scanning protocol determination module 516) may determine a scanning region of the object corresponding to each table position based on the scanning direction, the number of the one or more table positions, and/or a first predetermined relationship between a plurality of scanning regions of one or more objects and a plurality of corresponding table positions.

In some embodiments, the scanning region of the object may refer to a region of the object to be scanned by the imaging device. The scanning region may include one or more body parts of the object, for example, a head, a foot, a chest, an abdomen, an organ (e.g., a brain, a lung, a liver, a stomach, a rib, a vertebra, etc.), or the like, or any combination thereof. In some embodiments, the first predetermined relationship may be denoted by a first lookup chart.

In some embodiments, the first lookup chart may illustrate the relationship between the body length of the object, the number of one or more table positions for scanning the object, and the lengths of a plurality of body parts (e.g., the head, the trunk, the lower limb, etc.). Exemplary statistical values of the ratio of human leg to human body (i.e., perineal height/height*100) may be shown in Table 1. Exemplary statistical values of the ratio of human body to human head (i.e., height/head height*100) may be shown in Table 2.

TABLE 1

Statistical values of the ratio of human leg to human body

|  | Male | Female |
|---|---|---|
| Asian | 45.70 | 44.90 |
| European AND American | 47.68 | 47.34 |

TABLE 2

Statistical values of the ratio of human body to human head

|  | Male | Female |
|---|---|---|
| Asian | 7.18 | 6.95 |
| European AND American | 7.57 | 7.49 |

In some embodiments, a relationship between the required number of table positions and the height of the object (i.e., the body length of the object) may be established based on Equation (2). Assuming that the length of each scanning region of the scanning table is 320 mm, the initial length of an overlapping region of the scanning table at two adjacent table positions is 25%, an exemplary relationship between the required number of table positions and the height of the object may be determined as Table 3.

TABLE 3

Required number of table positions corresponding to different heights of objects

| The Required Number of Table Positions | Height Range (cm) |
|---|---|
| 1 | (0, 32] |
| 2 | (32, 56] |
| 3 | (56, 80] |
| 4 | (80, 104] |
| 5 | (104, 128] |
| 6 | (128, 152] |
| 7 | (152, 176] |
| 8 | (176, 200] |
| 9 | (200, 224] |

The relationship between the body length of the object, the number of one or more table positions for scanning the object, and the lengths of different body parts (i.e., the first lookup chart) may be obtained based on Equation (2), Table1, Table2 and Table 3. Taking asian man as an example, an exemplary relationship may be shown in Table 4. Table 4 may be designated as the first lookup chart. In some embodiments, the relationship between the body length of the object and the lengths of different body parts may be designated as a predetermined body proportions model.

TABLE 4

An exemplary relationship between the body length of the object, the number of one or more table positions for scanning the object, and the lengths of different body parts

| The Number of Table Positions | Height Range (cm) | Head (cm) | Trunk (cm) | Lower Limb (cm) |
|---|---|---|---|---|
| 1 | (0, 32] | (0, 4.46] | (0, 12.92] | (0, 14.62] |
| 2 | (32, 56] | (4.46, 7.80] | (12.92, 22.61] | (14.62, 25.59] |
| 3 | (56, 80] | (7.80, 11.14] | (22.61, 32.30] | (25.59, 36.56] |
| 4 | (80, 104] | (11.14, 14.48] | (32.30, 41.99] | (36.56, 47.53] |
| 5 | (104, 128] | (14.48, 17.83] | (41.99, 51.67] | (47.53, 58.50] |
| 6 | (128, 152] | (17.83, 21.17] | (51.67, 61.37] | (58.50, 69.46] |
| 7 | (152, 176] | (21.17, 24.51] | (61.37, 71.06] | (69.46, 80.43] |
| 8 | (176, 200] | (24.51, 27.86] | (71.06, 80.74] | (80.43, 91.40] |
| 9 | (200, 224] | (27.86, 31.20] | (80.84, 90.43] | (91.40, 102.37] |

Merely by way of example, a whole body scanning may be performed on an asian man with a height of 170 cm. Based on Table 4, seven table positions may be needed. Assuming that the initial length of the overlapping region of the scanning table at two adjacent table positions is 25%, $L_h$ and $L_f$ are 3 cm, if the scanning direction is from the head to the foot (or feet) of the asian man, the first table position may correspond to the head of the asian man, the last three table positions may correspond to the lower limb of the asian man, the second table position may correspond to the chest of the asian man, the third table position may correspond to the belly of the asian man, and the fourth table position may correspond to the pelvic cavity of the asian man. According to Table 4 or Table 2, the head length of the asian man may be 23.68 cm, and may be 26.68 cm after $L_h$ is added. According to Table 4 or Table 2, the length of the lower limb of the asian man may be 77.69 cm, and may be 80.69 cm after $L_f$ is added. The parameter $L_h$ may refer to the distance between the head of the asian man and the boundary of the scanning region of the scanning table located at the corresponding table position (i.e., the first table position). The parameter $L_f$ may refer to the distance between the foot of the asian man and the boundary of the scanning region of the scanning table located at the corresponding table position (i.e., the last table position).

In some embodiments, the overlapping region of the scanning table at two adjacent table positions may be automatically adjusted based on the effective value of the overlapping region. More descriptions of the effective value of the overlapping region may be found elsewhere in the present disclosure (e.g., FIG. 18 and the descriptions thereof).

In 1607, the processing device 140 (e.g., the scanning protocol determination module 516) may set a scanning protocol at each table position based on the scanning region of the object corresponding to the each table position. In some embodiments, each body part may have a corresponding scanning protocol determined by a large amount of testing. In some embodiments, some information of the scanning protocols corresponding to different body parts may be added, deleted, and/or modified. In some embodiments, a scanning protocol may include MR scanning protocols and corresponding parameters. Using automatic setting of scanning protocol(s), the workload of the operating technician may be reduced, improving the scanning efficiency, and thus reducing damage to the object being scanned, avoiding the impact of misoperation and/or experiences, and effectively improving scanning accuracy.

For the same type of objects, for example, asian men between the age of 25 and 30, the same part of the bodies may have a certain similarity. An optimal scanning protocol may be obtained by statistically analyzing the scanning protocols that has been applied for the part. Alternatively, the optimal scanning protocol may be obtained based on a plurality of experimental data. For a new similar object, for example, a 28 aged asian man, the optimal scanning protocol may be applied to scan the object. In some embodiments, the scanning protocol determination module 516 may determine the scanning protocol for each table position based on the optimal scanning protocols for the scanning regions of the object. In some embodiments, the scanning protocol may include a plurality of scanning parameter(s) and/or reconstruction parameter(s). For example, the scanning protocol may include but not limited to repetition time (TR), echo time (TE), inversion time (TI), number of excitation (NEX), acquisition time (TA), slice thickness, slice gap, matrix, field of view (FOV), flip angle, or the like, or any combination thereof. In some embodiments, the optimal scanning protocols may be stored in the storage 150 and/or an external data source. In some embodiments, the scanning protocol determination module 516 may obtain the optimal scanning protocols by accessing the storage 150 and/or the external data source. More descriptions regarding the setting of the scanning protocol may be found elsewhere in the present disclosure (e.g., FIG. 17 and the descriptions thereof).

It should be noted that the above description of the process 1600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 17:
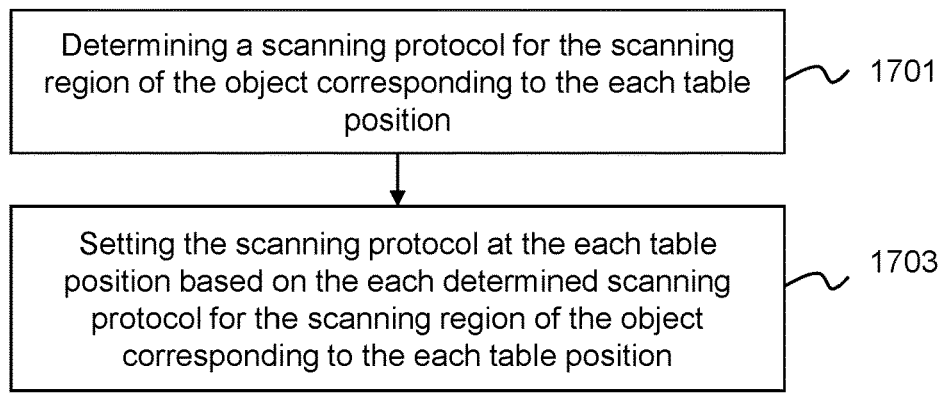
FIG. 17 is a flowchart illustrating an exemplary process for setting a scanning protocol at each table position according to some embodiments of the present disclosure.

FIG. 17 is a flowchart illustrating an exemplary process for setting a scanning protocol at each table position according to some embodiments of the present disclosure. In some embodiments, one or more operations of process 1700 may be implemented in the imaging system 100 illustrated in FIG. 1 or the imaging system 400 illustrated in FIG. 4. For example, the process 1700 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1700 may be implemented on the imaging device of the imaging system 100 or the imaging system 400. The operations of the illustrated process presented below are intended to be illustrative. In some embodiments, the process 1700 may be accomplished with one or more additional operations not described, and/or without one or more of the operations discussed. Additionally, the order in which the operations of the process 1700 as illustrated in FIG. 17 and described below is not intended to be limiting. In some embodiments, operation 1607 illustrated in FIG. 16 may be performed according to the process 1700.

In 1701, the processing device 140 (e.g., the scanning protocol determination module 516) may determine a scanning protocol for the scanning region of the object corresponding to the each table position.

In some embodiments, the scanning protocol determination module 516 may determine the scanning protocol based on the scanning region of the object corresponding to the each table position, and a second predetermined relationship between a plurality of scanning regions of one or more objects and a plurality of corresponding scanning protocols.

For a scanning region of an object (e.g., the chest), there may be a large amount of scans performed on the same scanning region of other object(s). Each scanning may have a corresponding scanning protocol. By analyzing the parameters of the scanning protocols, a universal scanning protocol corresponding to the scanning region may be obtained. The universal scanning protocol may be applied to scan the scanning region of new object(s). Because the universal scanning protocol is suitable for scanning the same part of any object, it may also be referred to as an optimal scanning protocol. Alternatively, the universal scanning protocol corresponding to a certain scanning region may be determined through a plurality of experiments. Each scanning region of the object may have a corresponding universal scanning protocol. In some embodiments, the second predetermined relationship may be denoted by a second lookup chart. The second lookup chart may be established based on the scanning regions of the object and corresponding universal scanning protocols. In some embodiments, for a same scanning region, it may have one or more corresponding universal scanning protocols. For example, the universal scanning protocols corresponding to the chests of children, adult men, and adult women may be different. In some embodiments, the data of the second lookup chart may be modified if needed. For example, the universal scanning protocols may be updated based on new historical scanning records. In some embodiments, the scanning protocol determination module 516 may determine the scanning protocol for the each scanning region of the object by looking up the second lookup chart directly.

In 1703, the processing device 140 (e.g., the scanning protocol determination module 516) may set the scanning protocol at the each table position based on the each determined scanning protocol for the scanning region of the object corresponding to the each table position.

Figure 18:
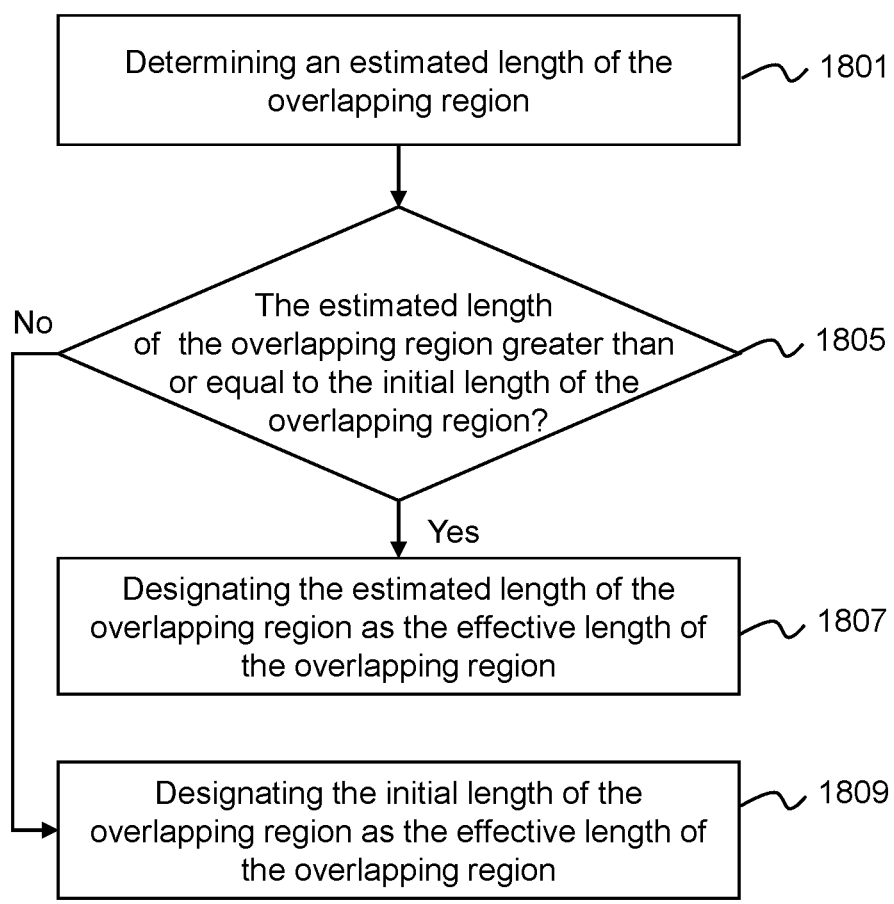
FIG. 18 is a flowchart illustrating an exemplary process for setting a scanning protocol at each table position according to some embodiments of the present disclosure.

FIG. 18 is a flowchart illustrating an exemplary process for setting a scanning protocol at each table position according to some embodiments of the present disclosure. In some embodiments, one or more operations of process 1800 may be implemented in the imaging system 100 illustrated in FIG. 1 or the imaging system 400 illustrated in FIG. 4. For example, the process 1800 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1800 may be implemented on the imaging device of the imaging system 100 or the imaging system 400. The operations of the illustrated process presented below are intended to be illustrative. In some embodiments, the process 1800 may be accomplished with one or more additional operations not described, and/or without one or more of the operations discussed. Additionally, the order in which the operations of the process 1800 as illustrated in FIG. 18 and described below is not intended to be limiting. In some embodiments, operation 1505 illustrated in FIG. 15 may be performed according to the process 1700.

In 1801, the processing device 140 (e.g., the overlapping region adjustment module 514) may determine an estimated length of the overlapping region.

In some embodiments, the estimated length may be a reference value for determining whether the initial length of the overlapping region of the scanning table at two adjacent table positions satisfies a certain condition (e.g., whether most of the scanning region (e.g., 80% or more) of the scanning table at each table position is covered by the scanning region of the object). The estimated length may be determined based on the number of the one or more table positions, the body length of the object, and/or the length of each scanning region of the scanning table, a first distance between a head of the object and an end of a corresponding table position, and a second distance between a foot of the object and an end of another corresponding table position.

Specifically, in a scanning process, it may be required that there is a distance between the head (and foot) of the object and the boundary of the scaning region of the scanning table located at the first table position (and the last table position), respectively. In some embodiments, the distance between the head of the object and the boundary of the scanning region of the scanning table located at the corresponding table position (i.e., the first table position) may be denoted by $L_h$. In some embodiments, the distance between the foot of the object and the boundary of the scanning region of the scanning table located at the corresponding table position (i.e., the last table position) may be $L_f$. In some embodiments, the length of the overlapping region of the scanning table at two adjacent table positions overlap (e.g., the estimated length) may satisfy Equation (3):

$$\text{couchsize} * \text{length} - \text{length} * \text{overlap}(\text{couchsize}-1) = \text{height} + L_h + L_f \qquad (3)$$

In some embodiments, the length of the overlapping region of the scanning table at two adjacent table positions overlap (e.g., the estimated length) may be determined according to Equation (4):

$$\text{overlap} = \frac{\text{couchsize} * \text{length} - \text{height} - L_h - L_f}{\text{length}(\text{couchsize} - 1)}. \qquad (4)$$

In 1805, the processing device 140 (e.g., the overlapping region adjustment module 514) may determine whether the estimated length of the overlapping region is greater than or equal to the initial length of the overlapping region. In some embodiments, if the estimated length of the overlappingregion is greater than or equal to the initial length of the overlapping region, the process 1800 may proceed to 1807. Otherwise, the process may proceed to 1809.

In 1807, the processing device 140 (e.g., the overlapping region adjustment module 514) may designate the estimated length of the overlapping region as the effective length of the overlapping region. If the estimated length of the overlapping region is greater than or equal to the initial length of the overlapping region, it may be indicated that the scanning region of the scanning table at the first position and/or the last position may not be covered by the most of the scanning region of the object. The overlapping region may need to be adjusted to make the scanning region of the scanning table at each table position to be covered by the scanning region of the object as much as possible.

In 1809, the processing device 140 (e.g., the overlapping region adjustment module 514) may designate the initial length of the overlapping region as the effective length of the overlapping region. If the estimated length of the overlapping region is smaller than the initial length of the overlapping region, it may be indicated that the initial length of the overlapping region may have already satisfied the condition, i.e., the scanning region of the scanning table at each table position is covered by most of the scanning region of the object. Therefore, the length of the overlapping region may not need to be adjusted.

It should be noted that the above description of the process 1800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 19:
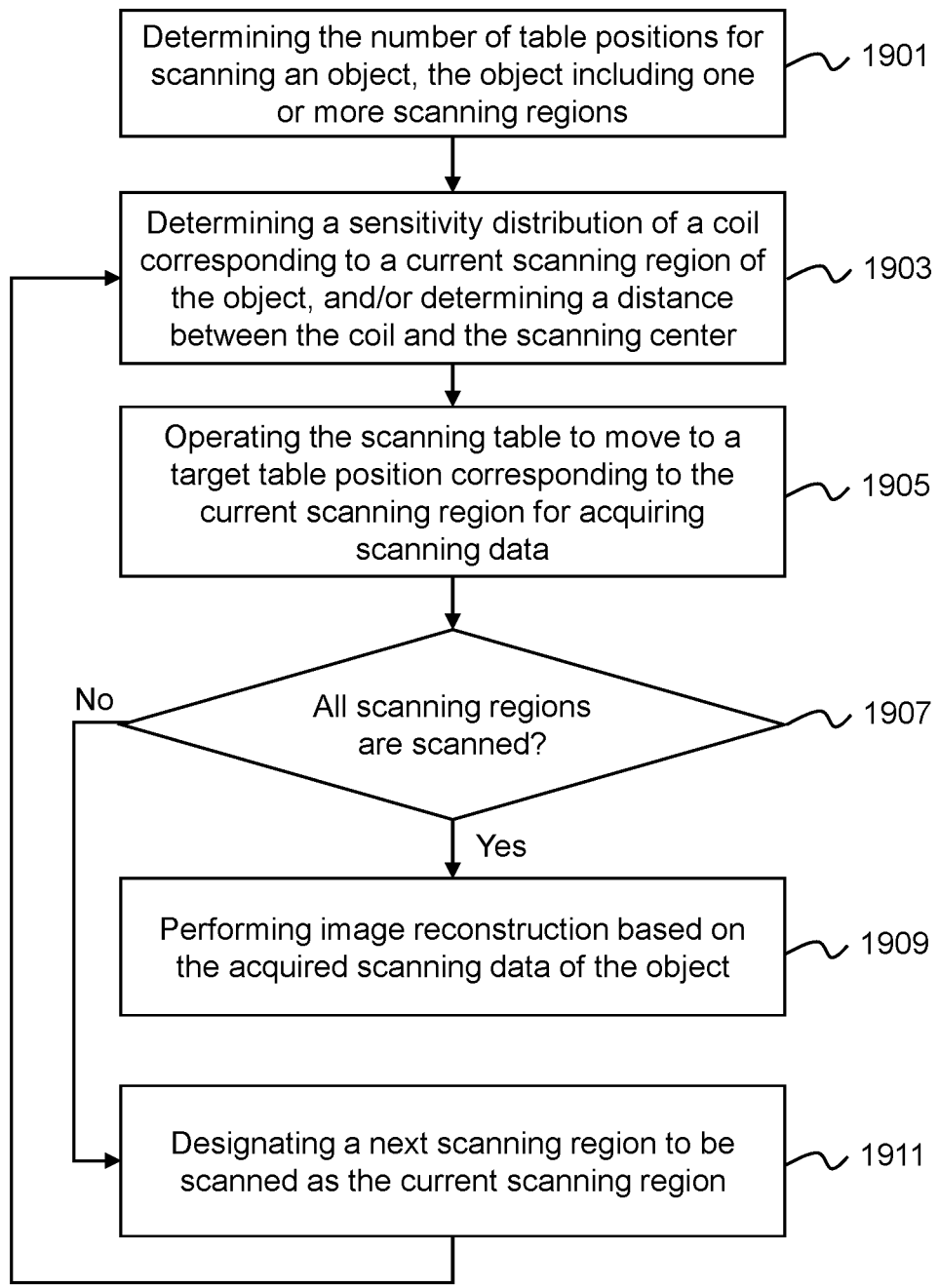
FIG. 19 is a flowchart illustrating an exemplary process for scanning an object according to some embodiments of the present disclosure.

FIG. 19 is a flowchart illustrating an exemplary process for scanning an object according to some embodiments of the present disclosure. In some embodiments, one or more operations of process 1900 may be implemented in the imaging system 100 illustrated in FIG. 1 or the imaging system 400 illustrated in FIG. 4. For example, the process 1900 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 5, or the like). As another example, a portion of the process 1900 may be implemented on the imaging device (e.g., a PET-MRI scanner) of the imaging system 100 or the imaging system 400. The operations of the illustrated process presented below are intended to be illustrative. In some embodiments, the process 1900 may be accomplished with one or more additional operations not described, and/or without one or more of the operations discussed. Additionally, the order in which the operations of the process 1900 as illustrated in FIG. 19 and described below is not intended to be limiting.

In 1901, the processing device 140 (or the table position number determination module 512) may determine the number of table positions for scanning the object. In some embodiments, the object may include one or more scanning regions, for example, a head, a foot, a chest, an abdomen, an organ (e.g., a brain, a lung, a liver, a stomach, a rib, a vertebra, etc.), or the like, or any combination thereof. In some embodiments, the scanning region located in the field of view of the image device 110 (or the imaging device 400) may be fixed or limited, and the object may not be covered completely in one scanning. Therefore, the scanning table may need to be moved to different table positions to scan different scanning regions of the object (e.g., the whole body of the object), in which each table position may correspond to a scanning region of the object. That is, one or more table positions of the scanning table may be required to perform a whole body scan of the object. In some embodiments, different scanning regions (e.g., organs) of the object may be scanned at different table positions.

In some embodiments, before the determination of the number of the table positions, the processing device 140 may obtain a body length of the object. The body length of the object may be also referred to as the height of the object. In some embodiments, the information relating to the body length of the object may be registered in the imaging system 100 (or the imaging system 400) in advance. In some embodiments, the processing device 140 may obtain the information related to the object by accessing the storage 150 directly or via the network 120.

In some embodiments, the processing device 140 (or the table position number determination module 512) may determine the number of the table positions for scanning the object based on a length of each scanning region of the scanning table, an initial length of an overlapping region of the scanning table at two adjacent table positions, and/or the body length of the object. More descriptions of the determination of the number of the table positions may be found elsewhere in the present disclosure (e.g., FIGS. 14-18 and the descriptions thereof).

In 1903, the processing device 140 (or the sensitivity distribution determination module 504) may determine a sensitivity distribution of a coil corresponding to a current scanning region of the object, and/or determining a distance between the coil and the scanning center. The current scanning region, corresponding to one of the table positions, may refer to a scanning region to be scanned in a current scanning. The coil (e.g., a surface coil or one or more coil units thereof) may be bound to the current scanning region of the object.

In some embodiments, the sensitivity distribution may represent a relationship between an effective sensitivity value and a position of the surface coil. The effective sensitivity value may increase as the distance between the position of the surface coil and the scanning center decreases, and vice versa. The sensitivity distribution may be expressed in various forms, for example, a curve, a table, a chart, or the like, or any combination thereof. The processing 140 may determine the sensitivity distribution of the coil based on a scanning calibration sequence. The scanning calibration sequence may include a radio frequency pulse sequence and/or a gradient pulse sequence. The radio frequency pulse sequence may be used to perform a radio frequency excitation on the scanning region of the object (e.g., the patient) to generate corresponding magnetic resonance signal(s). The gradient pulse sequence may be used to locate the spatial localization code of the scanning region of the object. The processing device 140 (or the acquisition module 502) may acquire the scanning calibration sequence from the storage 150 or an external data source. In some embodiments, the coil (e.g., the surface coil) may include one or more coil units. The processing device 140 (or the sensitivity distribution determination module 504) may determine a first signal intensity distribution of each coil unit and a second signal intensity distribution of a volume coil of the imaging device based on the scanning calibration sequence, and determine the sensitivity distribution of the each coil unit by fusing the first signal intensity distribution of the each coil unit and the second signal intensity distribution. More descriptions of the determination of the sensitivity distribution may be found elsewhere in the present disclosure (e.g., FIGS. 6-7 and the descriptions thereof).

In some embodiments, the processing device 140 (e.g., the center position determination module 506) may determine a center position of the coil. In some embodiments, the center position of the coil may correspond to an effective maximum sensitivity. The effective maximum sensitivity may be determined based on the sensitivity distribution of the coil (e.g., the surface coil). The processing device 140 (or the center position determination module 506) may determine the center position of the coil based on the effective maximum sensitivity/sensitivities. In some embodiments, the coil (e.g., the surface coil) may include one coil unit. The sensitivity distribution of the one coil unit may reflect the ability of the one coil unit for receiving signals, and the ability of the one coil unit for receiving signals may have a certain relationship with the position of the one coil unit. Assuming that the sensitivity distribution of the one coil unit (i.e., the surface coil) is denoted by a curve, the sensitivity value corresponding to the highest point of the curve may be the maximum value (i.e., the effective maximum sensitivity). The position corresponding to the effective maximum sensitivity may be determined as the center position of the coil. In some embodiments, the coil (e.g., the surface coil) may include at least two coil units. A center position of each coil unit may be determined based on the sensitivity distribution. Similarly, assuming that the sensitivity distribution of each coil unit is denoted by a curve, the sensitivity value corresponding to the highest point of the curve may be the maximum value (i.e., the effective maximum sensitivity) of the each coil unit. In some embodiments, the position corresponding to the effective maximum sensitivity of each coil unit may be determined as the center position of the coil. The center position of the coil (e.g., the surface coil) may be determined based on the center positions of the coil units. For example, the center position of the coil (e.g., the surface coil) may be determined as an average position of the center positions of the at least two coil units. More descriptions of the determination of the center position of the coil (e.g., the surface coil) may be found elsewhere in the present disclosure (e.g., FIGS. 8-9 and the descriptions thereof). In some embodiments, the distance between the coil (e.g., the center position of the coil) and the scanning center may be determined.

In 1905, the processing device 140 (e.g., the table position determination module 508) may operate the scanning table to move to a target table position corresponding to the current scanning region for acquiring scanning data. In some embodiments, the processing device 140 may determine a target table position corresponding to the current scanning region for acquiring scanning data. The target table position may correspond to the center position of the coil bounded to the current scanning region when the center position of the coil is located coincident with a scanning center of the imaging device (e.g., a PET-MRI scanner). More descriptions of the determination of target table position(s) may be found elsewhere in the present disclosure (e.g., FIGS. 6-13 and the descriptions thereof). In some embodiments, after determining the number of the table positions and/or the target table position(s), the scanning table may be automatically moved along a longitudinal axis of the scanner of the imaging device (e.g., a PET-MRI scanner) to one or more target table positions for scanning different scanning regions of the object.

In some embodiments, the processing device 140 (or the table position determination module 508) may determine a direction from the center position of the surface coil to the scanning center, based on the center position of the surface coil and the position of the scanning center. The coil (e.g., the surface coil) may be moved for the distance along the direction until the center position of the surface coil is located coincident with the scanning center. If the surface coil is located coincident with the scanning center, the position of the scanning table may coincident with the target position of the scanning table.

In some embodiments, the processing device 140 may set a scanning protocol at each target table position based on the scanning region of the object corresponding to the each target table position. In some embodiments, after moving the scanning table to the target position, a scanning for the current scanning region of the object may be performed. For example, one or more MR scans of a sequence of MR scans may be performed, and the scanning data may be acquired by the imaging device (e.g., a PET-MRI scanner). The sequence of MR scans may be stored in, for example, the storage 150 or an external source, in advance. In some embodiments, the processing device 140 may acquire the sequence of MR scans by accessing the storage 150 or the external source via the network 120. In some embodiments, the scanning data generated by the scan(s) may be stored in, for example, the storage 150 or an external source for further use. More descriptions of the process for scanning the object at each target table position may be found elsewhere in the present disclosure (e.g., FIGS. 16-18 and the descriptions thereof).

In 1907, the processing device 140 may determine whether all the scanning regions of the object are scanned. In some embodiments, if all the scanning regions of the object are scanned, the process 1900 may proceed to 1909. Otherwise, the process 1900 may proceed to 1911.

In 1909, the processing device 140 may perform image reconstruction based on the acquired scanning data of the object. In some embodiments, the image reconstruction operation may be performed based on one or more reconstruction algorithms including, for example, filtered back-projection, iterative reconstruction (e.g., ordered subsets iterative reconstruction), or the like. In 1911, the processing device 140 may designate a next scanning region that has not been scanned (and/or to be scanned) as the current scanning region. In some embodiments, operations 1903, 1905, and 1907 may be repeated for one or more times until all the scanning regions of the object are scanned. It should be noted that in some embodiments, after each scanning region of the object is scanned, one or more images of the scanning region may be reconstructed, and then a whole body image may be generated based on the one or more images.

Merely by way of example, if the whole body of the object needs to be scanned, the processing device may determine the number of table positions for scanning the object based on a length of each scanning region of the scanning table, an initial length of an overlapping region of the scanning table at two adjacent table positions, and/or the body length of the object. If the number of table positions for scanning the whole body of the object is three (i.e., there are three target table positions), and a scanning region is planned to be scanned at each table position, then at least one surface coil (or coil unit) may be bound to each scanning region of the object. There may be three scanning regions needs to be scanned, and a first scanning region may be designated as a current scanning region. A first center position of a first surface coil (or coil unit(s)) bound to the current scanning region (i.e., the first scanning region) of the object may be determined based on a sensitivity distribution of the first surface coil (or coil unit(s)); a first target table position of the scanning table may be determined based on the first center position; the scanning table may be operated to move to the first target table position; and the current scanning region (i.e., the first scanning region) may be scanned and a first set of scanning data may be obtained. There may be two scanning regions needs to be scanned, and a next scanning region (e.g., a second scanning region) may be designated as the current scanning region. Then a second center position of a second surface coil (or coil unit(s)) bound to the second scanning region (i.e., the second scanning region) of the object may be determined based on a sensitivity distribution of the second surface coil (or coil unit(s)); a second target table position of the scanning table may be determined based on the second center position; the scanning table may be operated to move to the second target table position; the current scanning region (e.g., the second scanning region) may be scanned and a second set of scanning data may be obtained. There may be one scanning region needs to be scanned, and a next scanning region (i.e., a third scanning region) may be designated as the current scanning region. Then a third center position of a third surface coil (or coil unit(s)) bound to the current scanning region (i.e., the third scanning region) of the object may be determined based on a sensitivity distribution of the third surface coil (or coil unit(s)); a third target table position of the scanning table may be determined based on the current center position (i.e., the third scanning region); the scanning table may be operated to move to the third target table position; the current scanning region (i.e., the third scanning region) may be scanned and a third set of scanning data may be obtained. After all the three scanning regions are scanned, the first set of scanning data, the second set of scanning data, and/or the third set of scanning data may be used to reconstruct one or more images of the object.

In some embodiments, a process for operating a combined PET-MRI scanner may include one or more of the following operations: determining the number (or count) of a plurality of table positions for scanning the object; obtaining a scanning calibration sequence of MRI scanning; determining, based on the scanning calibration sequence, a sensitivity distribution of a surface coil placed on the object; determining a center position of the surface coil based on the sensitivity distribution; and determining, based on the center position of the surface coil, the target position of at least one of the plurality of table positions. In some embodiments, the target position may correspond to the center position of the surface coil when the center position of the surface coil is located coincident with a scanning center of the imaging device. In some embodiments, the determination of a plurality of table positions for scanning the object may include one or more of the following operations: obtaining a body length of an object; and determining the number of table positions for scanning the object based on a length of each scanning region of the scanning table, an initial length of an overlapping region of the scanning table at two adjacent table positions, and the body length of the object. In some embodiments, various table positions may be generated when the scanning table is automatically moved along a longitudinal axis of the combined PET-MRI scanner. In some embodiments, the process may further include acquiring at least one of the MR scans of the sequence of MR scans at each of the table positions.

As illustrated above, one or more target table positions for scanning an object may be determined. The target table positions may be customized for the object. In some embodiments, an optimal number (or count) of the target table positions may be determined according to the body size (e.g., height, weight, or the like) of the object. Therefore, the determination of the number of the target table positions may be self-adapting, and the adaptability may be strong. According to the optimized number (or count) of target table positions, for each target table position of the scanning table, a sensitivity distribution of a coil used in MR scanning may be determined, and the each target position may be determined based on the sensitivity distribution of the coil. The scanning table may be moved to the target position for scanning the object. Therefore, the accuracy of the scanning table positioning may be improved by using the operations mentioned above, especially in a whole body scanning of a multimodality imaging device (e.g., a PET-MRI scanner). The process(es) illustrated in the present disclosure may have relatively high adaptability, and/or relatively high positioning accuracy. Meanwhile, upon the optimized number (or count) of the target table positions being determined, one or more scanning protocols (e.g., a PET scanning protocol, an MRI scanning protocol, or the like) may be automatically determined based on the number (or count) of the target table positions. Therefore, manual adjustment of the scanning protocol(s) by the user (e.g., a doctor) of the imaging device may be skipped. The workload of the user may be reduced. Besides, for a multimodality imaging device (e.g., a PET-MRI scanner), the registration accuracy of PET image(s) and MRI image(s) obtained at each table position may be improved, and accordingly, the misregistration between PET image(s) and MRI image(s) during subsequent operations may be reduced. Therefore, the accuracy of the reconstructed image (e.g., PET image(s) reconstructed based on the MRI image(s)) may be improved.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one computing device, each of which has at least one processor and a storage for positioning a scanning table, the method comprising:
obtaining a body length of an object; and
determining the number of table positions for scanning the object based on a length of each scanning region of the scanning table, an initial length of an overlapping region of the scanning table at two adjacent table positions, and the body length of the object.

2. The method of claim 1, further comprising:
determining an effective length of the overlapping region of the scanning table at two adjacent table positions based on the number of the table positions and the body length of the object; and
adjusting the overlapping region of the scanning table at two adjacent table positions based on the effective length of the overlapping region.

3. The method of claim 2, further comprising:
obtaining positioning information of the object on the scanning table;
determining a scanning direction for scanning the object based on the positioning information;
determining a scanning region of the object corresponding to each table position based on the scanning direction, the number of the table positions, and a first predetermined relationship between a plurality of scanning regions of one or more objects and a plurality of corresponding table positions; and
setting a scanning protocol at each table position based on the scanning region of the object corresponding to the each table position.

4. The method of claim 3, wherein the predetermined relationship between a plurality of scanning region of one or more objects and a plurality of corresponding table positions is denoted by a first lookup chart.

5. The method of claim 4, wherein the first lookup chart includes a correspondence between the body length of the object, the number of the table positions, and a length of each scanning region of the object.

6. The method of claim 4, wherein the setting a scanning protocol at each table position based on the scanning region of the object corresponding to the each table position comprises:
determining a scanning protocol for the scanning region of the object corresponding to the each table position based on the scanning region of the object corresponding to the each table position, and a second predetermined relationship between a plurality of scanning regions of one or more objects and a plurality of corresponding scanning protocols; and
setting the scanning protocol at the each table position based on the each determined scanning protocol for the scanning region of the object corresponding to the each table position.

7. The method of claim 6, wherein the second predetermined relationship between a plurality of scanning regions of one or more objects and a plurality of corresponding scanning protocols is denoted by a second lookup chart.

8. The method of claim 2, wherein the determining an effective length of the overlapping region of the scanning table at two adjacent table positions based on the number of the table positions and the body length of the object comprises:
determining an estimated length of the overlapping region based on the number of the table positions, the body length of the object, the length of each scanning region of the scanning table, a first distance between a head of the object and an end of a corresponding table position, and a second distance between a foot of the object and an end of a corresponding table position; and
determining the effective length of the overlapping region based on the estimated length of the overlapping region or the initial length of the overlapping region.

9. The method of claim 8, wherein the determining the effective length of the overlapping region based on the estimated length of the overlapping region or the initial length of the overlapping region comprises:
determining whether the estimated length of the overlapping region is greater than or equal to the initial length of the overlapping region; and
in response to a determination that the estimated length of the overlapping region is greater than or equal to the initial length of the overlapping region, designating the estimated length of the overlapping region as the effective length of the overlapping region.

10. The method of claim 8, wherein the determining the effective length of the overlapping region based on the estimated length of the overlapping region or the initial length of the overlapping region comprises:
determining whether the estimated length of the overlapping region is greater than or equal to the initial length of the overlapping region; and
in response to the determination that the estimated length of the overlapping region is smaller than the initial length of the overlapping region, designating the initial length of the overlapping region as the effective length of the overlapping region.

11. The method of claim 1, wherein determining the number of table positions for scanning the object based on a length of a scanning region of the scanning table, an initial length of an overlapping region of the scanning table at two adjacent table positions, and the body length of the object comprises:
determining the number of the table positions for scanning the object based on the following equation:

$$couchsize = \text{ceil}\left(\frac{\text{height} + \text{length} * overlap_{min}}{\text{length} * (1 - overlap_{min})}\right)$$

wherein couchsize refers to the number of the table positions for scanning the object, the cell function refers to a determination of a minimum integer that is greater than or equal to $$\frac{\text{height} + \text{length} * overlap_{min}}{\text{length} * (1 - overlap_{min})},$$

height refers to the body length of the object, length refers to the length of each scanning region of the scanning table, and $overlap_{min}$ refers to the initial length of an overlapping region of the scanning table at two adjacent table positions.

12. A system for positioning a scanning table, comprising:
at least one storage device including a set of instructions or programs; and at least one processor configured to communicate with the at least one storage device, wherein when executing the set of instructions or programs, the at least one processor is configured to cause the system to:
- obtain a body length of an object; and
- determine the number of table positions for scanning the object based on a length of each scanning region of the scanning table, an initial length of an overlapping region of the scanning table at two adjacent table positions, and the body length of the object.

13. The system of claim 12, the at least one processor is further configured to cause the system to:
- determine an effective length of the overlapping region of the scanning table at two adjacent table positions based on the number of the table positions and the body length of the object; and
- adjust the overlapping region of the scanning table at two adjacent table positions based on the effective length of the overlapping region.

14. The system of claim 13, the at least one processor is further configured to cause the system to:
- obtain positioning information of the object on the scanning table;
- determine a scanning direction for scanning the object based on the positioning information;
- determine a scanning region of the object corresponding to each table position based on the scanning direction, the number of the table positions, and a first predetermined relationship between a plurality of scanning regions of one or more objects and a plurality of corresponding table positions; and
- set a scanning protocol at each table position based on the scanning region of the object corresponding to the each table position.

15. The system of claim 14, wherein the predetermined relationship between a plurality of scanning region of one or more objects and a plurality of corresponding table positions is denoted by a first lookup chart.

16. A method implemented on at least one computing device, each of which has at least one processor and a storage for determining a target position of a scanning table of an imaging device, the method comprising:
- obtaining a scanning calibration sequence;
- determining a sensitivity distribution of a surface coil of the imaging device based on the scanning calibration sequence;
- determining a center position of the surface coil based on the sensitivity distribution; and
- determining the target position of the scanning table based on the center position of the surface coil, the target position of the scanning table corresponding to the center position of the surface coil when the center position of the surface coil is located coincident with a scanning center of the imaging device.

17. The method of claim 16, wherein the surface coil includes at least one coil unit, and the determining a sensitivity distribution of a surface coil based on the scanning calibration sequence comprises:
- obtaining a first signal of each coil unit of the at least one coil unit generated based on the scanning calibration sequence;
- obtaining a second signal of a volume coil of the imaging device generated based on the scanning calibration sequence;
- determining a first signal intensity distribution of the each coil unit of the at least one coil unit based on the first signal;
- determining a second signal intensity distribution of the volume coil of the imaging device based on the second signal; and
- obtaining the sensitivity distribution of the each coil unit by fusing the first signal intensity distribution of the each coil unit and the second signal intensity distribution.

18. The method of claim 16, wherein the surface coil is used to be bound to an object to be scanned by the imaging device.

19. The method of claim 16, further comprising:
- obtaining scanning information relating to the object, the scanning information including a body length of the object and a scanning region of the object, the surface coil being configured to be bound to the scanning region of the object;
- determining an estimated target position of the scanning table based on the scanning information, the body length of the object, and a predetermined body proportions model; and
- operating the scanning table to move to the estimated target position.

20. The method of claim 16, further comprising:
- adjusting the scanning table from the estimated target position to the target position for scanning the object.

* * * * *